(12) United States Patent
Kobayashi

(10) Patent No.: US 11,154,263 B2
(45) Date of Patent: Oct. 26, 2021

(54) RADIOGRAPHY APPARATUS, RADIOGRAPHY APPARATUS OPERATION METHOD, AND RADIOGRAPHY APPARATUS OPERATION PROGRAM

(71) Applicant: FUJIFILM CORPORATION, Tokyo (JP)

(72) Inventor: Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 106 days.

(21) Appl. No.: 16/830,271

(22) Filed: Mar. 26, 2020

(65) Prior Publication Data

US 2020/0305818 A1    Oct. 1, 2020

(30) Foreign Application Priority Data

Mar. 29, 2019    (JP) .............................. JP2019-067605

(51) Int. Cl.
*A61B 6/00*    (2006.01)
*H01J 35/06*    (2006.01)

(52) U.S. Cl.
CPC ................ *A61B 6/482* (2013.01); *A61B 6/42* (2013.01); *A61B 6/44* (2013.01); *A61B 6/481* (2013.01); *A61B 6/5205* (2013.01); *A61B 6/548* (2013.01); *H01J 35/064* (2019.05)

(58) Field of Classification Search
CPC ....... A61B 6/482; A61B 6/548; A61B 6/5205; A61B 6/44; A61B 6/481; A61B 6/42; A61B 6/545; A61B 6/5235; A61B 6/542; A61B 6/06; A61B 6/0487; A61B 6/4007; A61B 6/465; A61B 6/467; A61B 6/5241; A61B 6/54; H01J 35/064; H01J 35/065; H05G 1/70

See application file for complete search history.

(56) References Cited

U.S. PATENT DOCUMENTS

| | | | | |
|---|---|---|---|---|
| 2004/0213377 A1* | 10/2004 | Endo | ...................... | A61B 6/482 378/98.11 |
| 2004/0247079 A1* | 12/2004 | Endo | ........................ | G01T 1/24 378/98.12 |
| 2006/0289774 A1* | 12/2006 | Endo | .................... | A61B 6/0478 250/370.09 |

FOREIGN PATENT DOCUMENTS

JP    2011-067333 A    4/2011

* cited by examiner

*Primary Examiner* — Courtney D Thomas
(74) *Attorney, Agent, or Firm* — Solaris Intellectual Property Group, PLLC

(57) ABSTRACT

An acquisition unit of a console acquires a first radiographic image and a second radiographic image. The first radiographic image and the second radiographic image are radiographic images which are output from a radiation detector by directing a radiation source to emit first radiation and second radiation in order to perform a moving image capture mode that continuously acquires a radiographic image required for the display of a moving image according to a preset frame interval. A receiving unit receives a request signal to request the generation of an energy subtraction image referred to for diagnosis. A generation unit generates the energy subtraction image in a case in which the receiving unit receives the request signal.

16 Claims, 26 Drawing Sheets

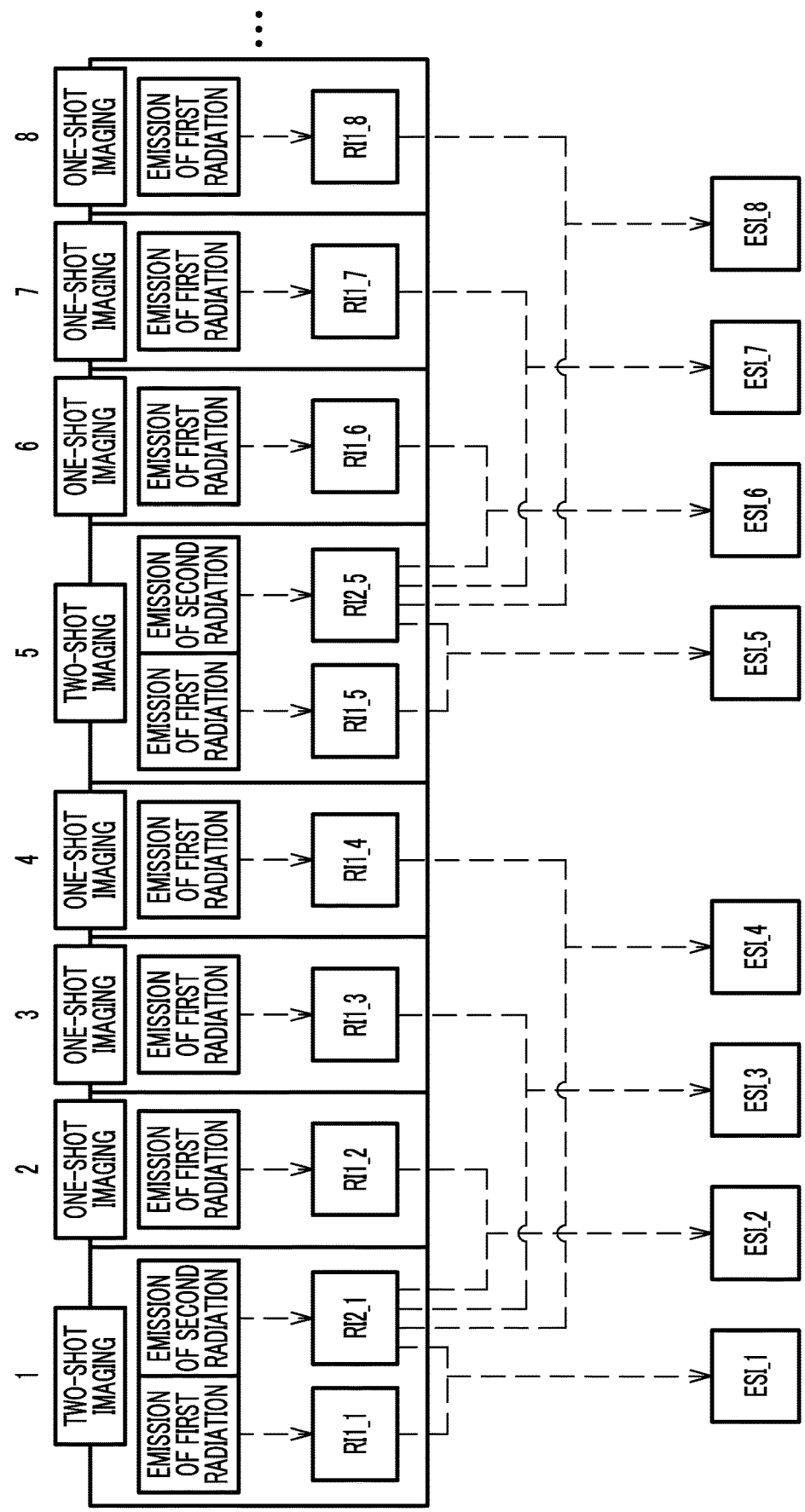

RADIOGRAPHY APPARATUS, RADIOGRAPHY APPARATUS OPERATION METHOD, AND RADIOGRAPHY APPARATUS OPERATION PROGRAM

CROSS-REFERENCE TO RELATED APPLICATIONS

The present application claims priority under 35 U.S.C. § 119 to Japanese Patent Application No. 2019-067605 filed on Mar. 29, 2019. The above application is hereby expressly incorporated by reference, in its entirety, into the present application.

BACKGROUND

1. Technical Invention

A technology of the present disclosure relates to a radiography apparatus, a radiography apparatus operation method, and a radiography apparatus operation program.

2. Description of the Related Art

In the field of medical radiography, radiography apparatuses have been known which perform energy subtraction (hereinafter, abbreviated to ES) imaging (for example, see JP2011-067333A). As described in JP2011-067333A, the ES imaging is an imaging method which directs a radiation source to continuously emit first radiation and second radiation having different energy distributions and directs a radiation detector to output a first radiographic image based on the first radiation and a second radiographic image based on the second radiation. Hereinafter, the ES imaging method that continuously emits the first radiation and the second radiation is referred to as two-shot imaging.

It is possible to generate an ES image in which a structure in a subject has been highlighted on the basis of the first radiographic image and the second radiographic image. Specifically, the pixel value of each of the first radiographic image and the second radiographic image is multiplied by an appropriate weighting coefficient and then the difference between the pixel values is calculated to generate an ES image. Examples of the structure include bone tissues, such as the ribs and the spine, and soft tissues such as the lung or the stomach.

SUMMARY

As described above, the ES imaging according to the related art is completed by performing the two-shot imaging operation once. Therefore, the ES image acquired by the ES imaging according to the related art is a so-called still image. In contrast, the inventors have conducted a study on, for example, a technique which continuously performs the two-shot imaging operation a plurality of times to continuously acquire a plurality of ES images required for displaying a moving image according to a preset frame interval.

However, even in a case in which a plurality of ES images are continuously acquired, in the actual diagnosis, it is considered that not all of the plurality of ES images but some of the plurality of ES images are selectively referred to. For this reason, there is a concern that a process for generating ES images other than the ES image to be referred to for diagnosis will be unnecessary.

An object of the technology of the present disclosure is to provide a radiography apparatus, a radiography apparatus operation method, and a radiography apparatus operation program that can effectively generate an energy subtraction image to be referred to for diagnosis.

In order to achieve the object, according to the present disclosure, there is provided a radiography apparatus comprising: a radiation source that emits radiation; a radiation detector that detects the radiation transmitted through a subject and outputs a radiographic image of the subject; a radiation source control unit that performs control to direct the radiation source to continuously emit the radiation in order to perform a moving image capture mode which continuously acquires a plurality of the radiographic images required for displaying a moving image according to a preset frame interval; a detector control unit that performs control to direct the radiation detector to continuously output the radiographic image based on the radiation in a case in which the moving image capture mode is performed; an acquisition unit that acquires the radiographic image; a receiving unit that receives a request signal to request generation of an energy subtraction image in which a structure in the subject has been highlighted and which is referred to for diagnosis; and a generation unit that generates the energy subtraction image on the basis of the radiographic image acquired by the acquisition unit during the moving image capture mode, does not generate the energy subtraction image in a case in which the receiving unit does not receive the request signal, and generates the energy subtraction image in a case in which the receiving unit receives the request signal.

Preferably, the moving image capture mode includes directing the radiation source to emit first radiation with a first energy distribution and second radiation with a second energy distribution different from the first energy distribution and directing the radiation detector to output a first radiographic image based on the first radiation and a second radiographic image based on the second radiation and the generation unit generates the energy subtraction image on the basis of the first radiographic image and the second radiographic image.

Preferably, the radiography apparatus according to the present disclosure further comprises a detection unit that detects whether or not a contrast agent has been administered to the subject and outputs the request signal to the receiving unit in a case in which it is detected that contrast agent has been administered.

Preferably, the radiography apparatus according to the present disclosure further comprises an operation unit that outputs the request signal to the receiving unit in response to an operation command from an operator.

Preferably, an average value of generation intervals of the energy subtraction image is greater than the frame interval.

Preferably, the radiography apparatus according to the present disclosure further comprises a display control unit that performs control to display the energy subtraction image and at least one of the first radiographic image or the second radiographic image.

Preferably, in the moving image capture mode, a one-shot imaging operation which directs the radiation source to emit only one of the first radiation and the second radiation and directs the radiation detector to output only one of the first radiographic image and the second radiographic image is performed in a case in which the receiving unit does not receive the request signal.

Preferably, in the moving image capture mode, a two-shot imaging operation which directs the radiation source to continuously emit the first radiation and the second radiation and directs the radiation detector to output the first radiographic image and the second radiographic image is performed in a case in which the receiving unit receives the request signal.

Preferably, in the moving image capture mode, the one-shot imaging operation and the two-shot imaging operation which directs the radiation source to continuously emit the first radiation and the second radiation and directs the radiation detector to output the first radiographic image and the second radiographic image are performed in a case in which the receiving unit receives the request signal.

Preferably, the generation unit generates the energy subtraction image corresponding to the two-shot imaging operation on the basis of the first radiographic image and the second radiographic image output from the radiation detector in the two-shot imaging operation and generates the energy subtraction image corresponding to the one-shot imaging operation on the basis of one of the first radiographic image and the second radiographic image output from the radiation detector in the one-shot imaging operation and the other of the first radiographic image and the second radiographic image output from the radiation detector in the two-shot imaging operation immediately before the one-shot imaging operation.

Preferably, an intensity of the second radiation in the second energy distribution is lower than an intensity of the first radiation in the first energy distribution and the radiation source control unit directs the radiation source to emit only the second radiation in the one-shot imaging operation.

Preferably, the radiation source includes a radiation tube having a cold cathode. Preferably, the cold cathode is a field emission type having an electron emission source that emits an electron beam using a field emission phenomenon.

Preferably, at least two radiation tubes of a first radiation tube that generates the first radiation and a second radiation tube that generates the second radiation are provided as the radiation tube.

There is provided a method for operating a radiography apparatus comprising a radiation source that emits radiation and a radiation detector that detects the radiation transmitted through a subject and outputs a radiographic image of the subject. The method comprises: a radiation source control step of performing control to direct the radiation source to continuously emit the radiation in order to perform a moving image capture mode which continuously acquires a plurality of the radiographic images required for displaying a moving image according to a preset frame interval; a detector control step of performing control to direct the radiation detector to continuously output the radiographic image based on the radiation in a case in which the moving image capture mode is performed; an acquisition step of acquiring the radiographic image; a receiving step of receiving a request signal to request generation of an energy subtraction image in which a structure in the subject has been highlighted and which is referred to for diagnosis; a generation step of generating the energy subtraction image on the basis of the radiographic image acquired in the acquisition step during the moving image capture mode and generating the energy subtraction image in a case in which the request signal is received in the receiving step; and a non-generation step of not generating the energy subtraction image in a case in which the request signal is not received in the receiving step.

There is provided a program for operating a radiography apparatus comprising a radiation source that emits radiation and a radiation detector that detects the radiation transmitted through a subject and outputs a radiographic image of the subject. The program causing a computer to function as: a radiation source control unit that performs control to direct the radiation source to continuously emit the radiation in order to perform a moving image capture mode which continuously acquires a plurality of the radiographic images required for displaying a moving image according to a preset frame interval; a detector control unit that performs control to direct the radiation detector to continuously output the radiographic image based on the radiation in a case in which the moving image capture mode is performed; an acquisition unit that acquires the radiographic image; a receiving unit that receives a request signal to request generation of an energy subtraction image in which a structure in the subject has been highlighted and which is referred to for diagnosis; and a generation unit that generates the energy subtraction image on the basis of the radiographic image acquired by the acquisition unit during the moving image capture mode, does not generate the energy subtraction image in a case in which the receiving unit does not receive the request signal, and generates the energy subtraction image in a case in which the receiving unit receives the request signal.

According to the technology of the present disclosure, it is possible to provide a radiography apparatus, a radiography apparatus operation method, and a radiography apparatus operation program that can effectively generate an energy subtraction image to be referred to for diagnosis.

BRIEF DESCRIPTION OF THE DRAWINGS

Exemplary embodiments according to the technique of the present disclosure will be described in detail based on the following figures, wherein:

FIG. 30 is a diagram illustrating an energy subtraction image generation method in a case in which not the second radiation but only the first radiation is emitted in the one-shot imaging operation.

DETAILED EMBODIMENTS

First Embodiment

Figure 1:
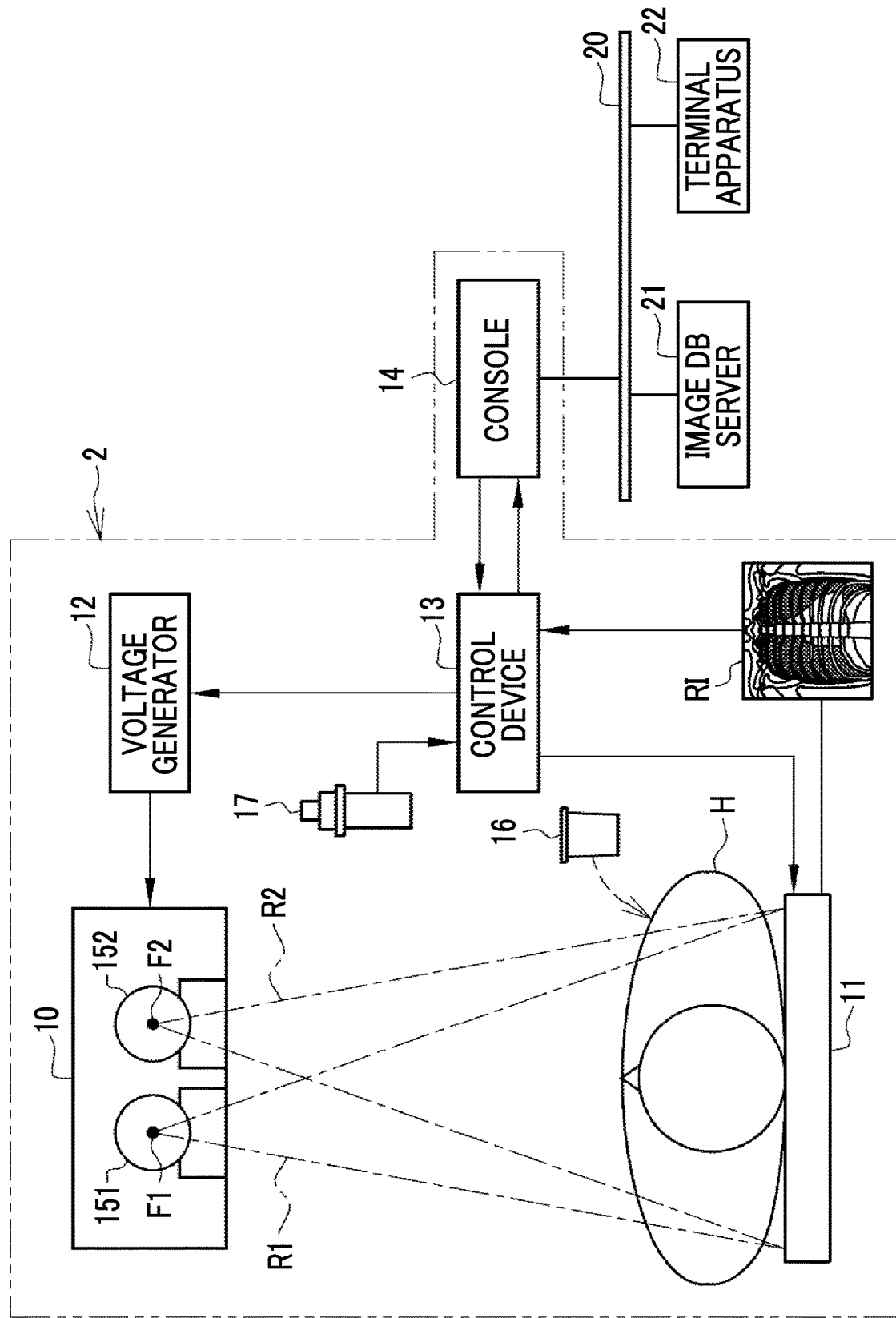
FIG. 1 is a diagram illustrating, for example, a radiography apparatus.

In FIG. 1, a radiography apparatus 2 comprises a radiation source 10, a radiation detector 11, a voltage generator 12, a control device 13, and a console 14. The radiation source 10, the radiation detector 11, the voltage generator 12, and the control device 13 are provided in, for example, a radiography room of a medical facility. The console 14 is provided in, for example, a control room adjacent to the radiography room. The radiography apparatus 2 is operated by an operator such as a radiology technician.

The radiation source 10 includes a first radiation tube 151 and a second radiation tube 152. The first radiation tube 151 generates first radiation R1 from a first focus F1. The second radiation tube 152 generates second radiation R2 from a second focus F2. Hereinafter, in some cases, the first radiation tube 151 and the second radiation tube 152 are collectively referred to as a "radiation tube 15". Similarly, in some cases, the first focus F1 and the second focus F2 are collectively referred to as a "focus F" and the first radiation R1 and the second radiation R2 are collectively referred to as "radiation R". The radiation R is, for example, X-rays or γ-rays.

The radiation detector 11 detects the radiation R transmitted through a subject H and outputs a radiographic image RI of the subject H. The radiation detector 11 transmits the radiographic image RI to the control device 13. FIG. 1 illustrates an aspect in which a contrast agent 16 is administered and a radiographic image of the chest of a subject H is captured.

The radiation detector 11 has an imaging surface on which pixels converting the radiation R into electric signals are two-dimensionally arranged. The radiation detector 11 performs an accumulation operation that accumulates signal charge based on the radiation R in the pixel and a reading operation that reads the signal charge from the pixel and converts the signal charge into an electric signal. The radiation detector 11 is called a flat panel detector (FPD). The radiation detector 11 may be an indirect conversion type that includes a scintillator converting the radiation R into visible light and converts the visible light emitted from the scintillator into an electric signal or a direct conversion type that directly converts the radiation R into an electric signal. Hereinafter, in some cases, the electric signal is referred to as a "pixel value".

The voltage generator 12 generates a tube voltage to be applied to the radiation tube 15. The voltage generator 12 and the radiation tube 15 are connected to each other by a voltage cable (not illustrated). The tube voltage generated by the voltage generator 12 is supplied to the radiation tube 15 through the voltage cable.

The control device 13 controls the operation of the radiation source 10 through the voltage generator 12. The console 14 transmits the irradiation conditions of the radiation R to the control device 13. The control device 13 sets the irradiation conditions in the voltage generator 12. The irradiation conditions include a tube voltage applied to the radiation tube 15, a tube current, and the irradiation time of the radiation R. Instead of the tube current and the irradiation time, a tube current-irradiation time product (a so-called mAs value) may be used as the irradiation condition.

The operator inputs a radiography start command to the control device 13 through an irradiation switch 17. In a case in which the start command is input, the control device 13 directs the radiation tube 15 to generate the radiation R under the set irradiation conditions. The irradiation switch 17 is provided in the control room together with the console 14.

The control device 13 also controls the operation of the radiation detector 11. The control device 13 directs the radiation detector 11 to perform the accumulation operation in synchronization with the timing when the radiation source 10 starts the emission of the radiation R. In addition, the control device 13 directs the radiation detector 11 to perform the reading operation in synchronization with the timing when the radiation source 10 ends the emission of the radiation R. Further, the control device 13 receives the radiographic image RI transmitted from the radiation detector 11. The control device 13 transmits the received radiographic image RI to the console 14.

The operator inputs irradiation conditions to the console 14. The console 14 transmits the input irradiation conditions to the control device 13. In addition, the console 14 receives the radiographic image RI transmitted from the control device 13.

The console 14 is connected to an image database (hereinafter, abbreviated to DB) server 21 through a network 20, such as a local area network (LAN), such that it can communicate with the image DB server 21. The image DB server 21 is, for example, a picture archiving and communication system (PACS) server, receives the radiographic image RI from the console 14, and accumulates and manages the radiographic image RI.

The terminal apparatus 22 is also connected to the network 20. The terminal apparatus 22 is, for example, a personal computer that is used by a doctor who makes a diagnosis with reference to the radiographic image RI. The terminal apparatus 22 receives the radiographic image RI from the image DB server 21 and displays the radiographic image RI on the display.

Figure 2:
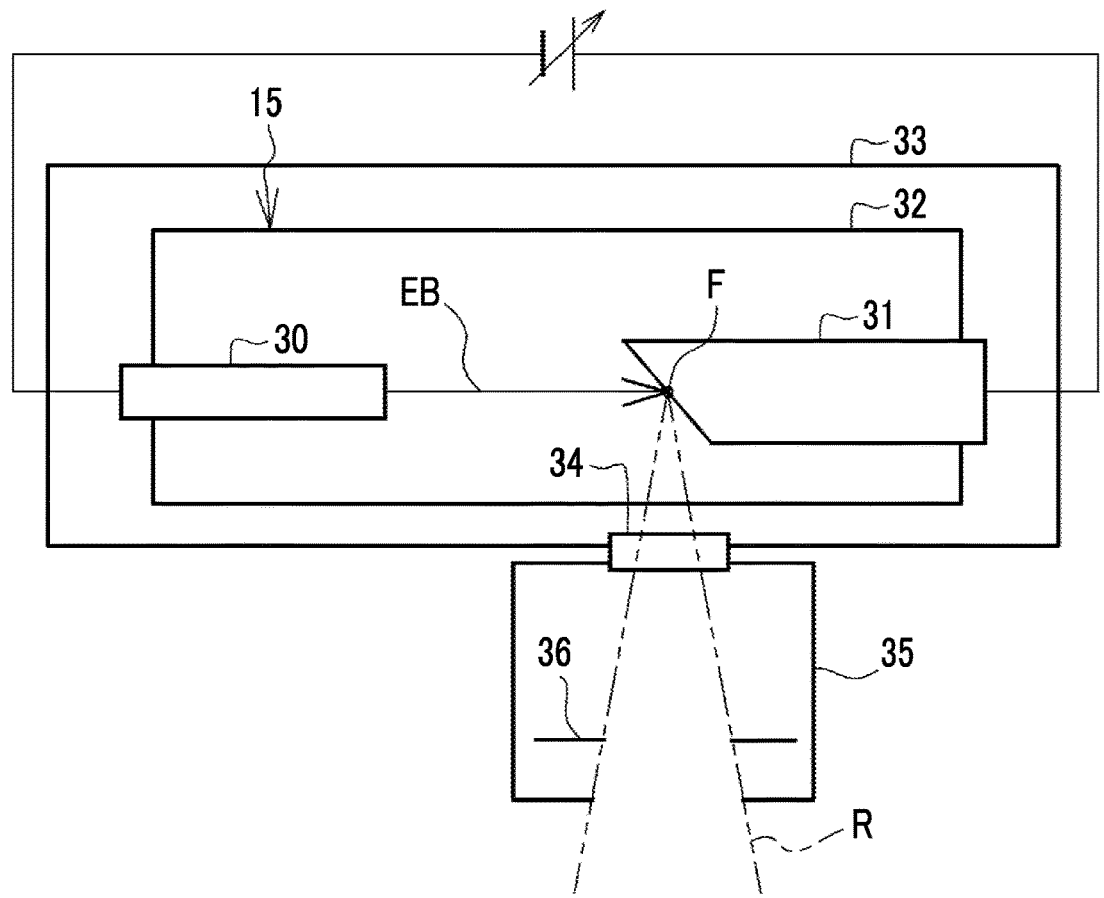
FIG. 2 is a diagram illustrating a radiation tube.

In FIG. 2, the radiation tube 15 includes a cathode 30 and an anode 31. The cathode 30 emits electrons. The electrons collide with the anode 31 and the anode 31 emits the radiation R. The cathode 30 and the anode 31 are accommodated in a vacuum glass tube 32 having a substantially cylindrical shape. The cathode 30 is a cold cathode. Specifically, the cathode 30 is a field emission type including an electron emission source that emits an electron beam EB to the anode 31, using a field emission phenomenon. The anode 31 is a fixed anode which is not rotated and whose position is fixed, unlike a rotating anode that is rotated by a rotation mechanism.

The voltage generator 12 applies a tube voltage between the cathode 30 and the anode 31. The electron beam EB is emitted from the cathode 30 to the anode 31 by the application of the tube voltage. Then, the radiation R is emitted from the focus F which is a point of the anode 31 where the electron beam EB collides.

The radiation tube 15 is accommodated in a housing 33. The housing 33 is provided with a radiation transmission window 34 that transmits the radiation R. The radiation R emitted from the anode 31 is emitted to the outside of the housing 33 through the radiation transmission window 34. In addition, the housing 33 is filled with insulating oil.

An irradiation field limiter 35 is provided in the radiation transmission window 34. The irradiation field limiter 35 is also called a collimator and sets the irradiation field of the radiation R in an imaging surface of the radiation detector 11. Specifically, the irradiation field limiter 35 includes a plurality of shielding plates 36 which are made of, for example, lead and shield the radiation R transmitted through the radiation transmission window 34. The shielding plates 36 are moved to change the size of, for example, a rectangular irradiation opening defined by the shielding plates 36, thereby setting the irradiation field of the radiation R.

Figure 3:
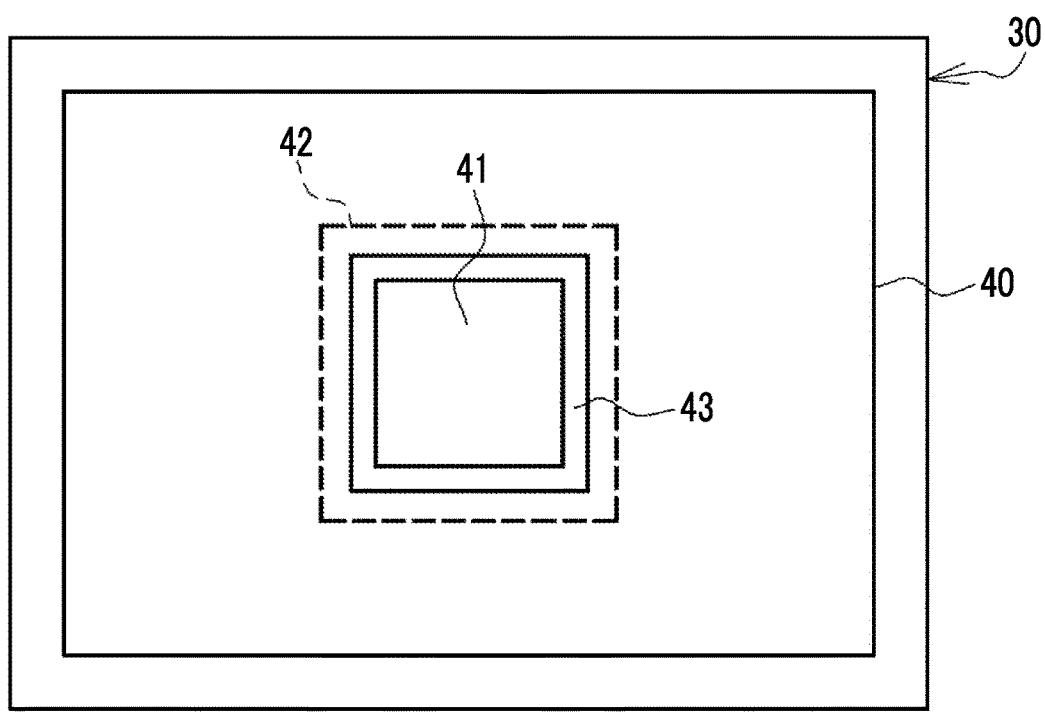
FIG. 3 is a diagram illustrating a cathode.

In FIG. 3, the cathode 30 has a structure in which an emitter electrode 41 and a gate electrode 42 are provided on a semiconductor substrate 40. The semiconductor substrate 40 is made of, for example, crystallized silicon. The emitter electrode 41 is, for example, a cone-shaped carbon nanotube. The emitter electrode 41 is connected to the gate electrode 42. The emitter electrode 41 functions as an emission area of the electron beam EB. That is, the emitter electrode 41 is an example of an "electron emission source" according to the technology of the present disclosure.

A focusing electrode 43 is provided around the emitter electrode 41. In a case in which a focusing voltage is applied to the focusing electrode 43, the electron beam EB emitted from the emitter electrode 41 is accelerated toward the anode 31 and is focused.

Figure 4:
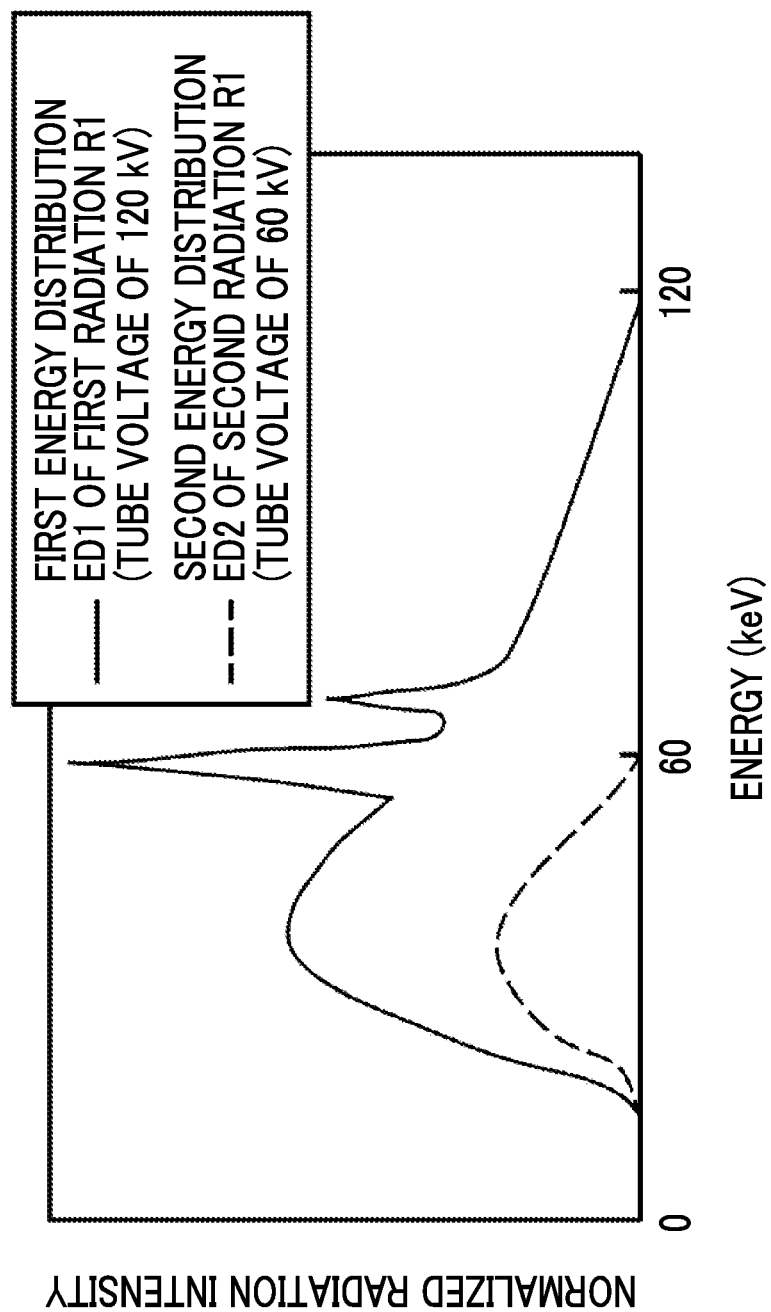
FIG. 4 is a graph illustrating a first energy distribution of first radiation and a second energy distribution of second radiation.

In FIG. 4, the first radiation R1 generated from the first radiation tube 151 has a first energy distribution ED1 represented by a solid line. In contrast, the second radiation R2 generated from the second radiation tube 152 has a second energy distribution ED2 represented by a dashed line. The first radiation R1 is generated by setting a tube voltage higher than the second radiation R2, for example, a tube voltage of 120 kV. The second radiation R2 is generated by setting a tube voltage lower than the first radiation R1, for example, a tube voltage of 60 kV. The intensity of the second radiation R2 in the second energy distribution ED2 is lower than the intensity of the first radiation R1 in the first energy distribution ED1 due to the difference between the tube voltage levels. In short, the second radiation R2 has lower energy than the first radiation R1. Hereinafter, in some cases, the first energy distribution ED1 and the second energy distribution ED2 are collectively referred to as an "energy distribution ED".

Figure 5:
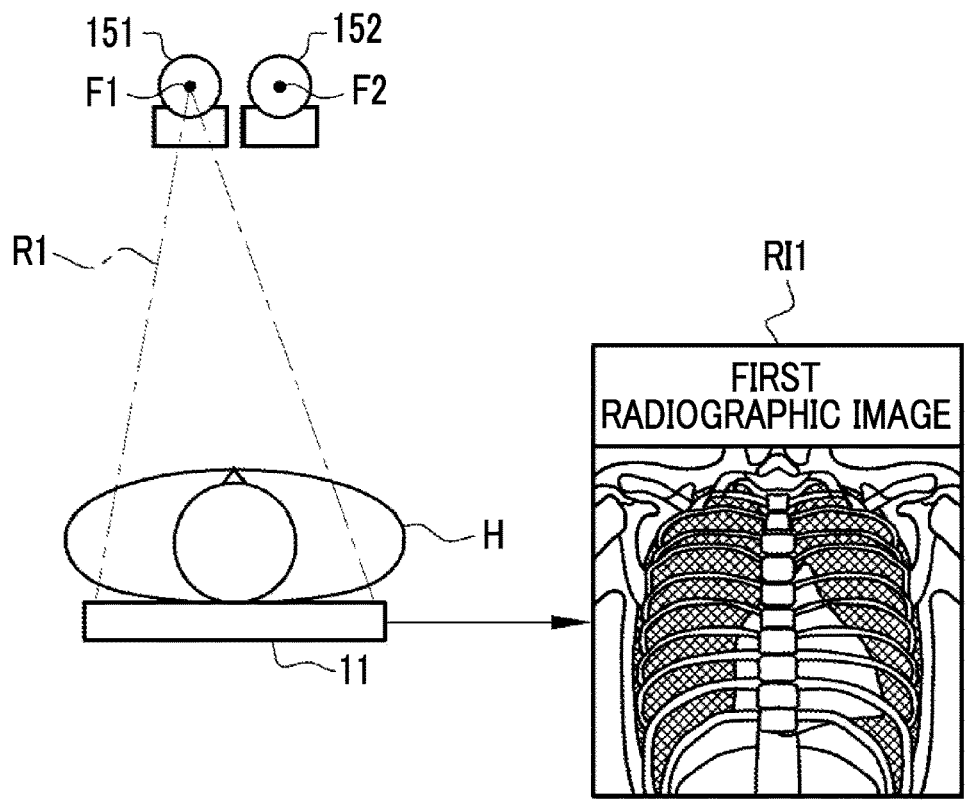
FIG. 5 is a diagram illustrating an aspect in which a first radiation tube generates the first radiation and a radiation detector outputs a first radiographic image based on the first radiation transmitted through a subject.
Figure 6:
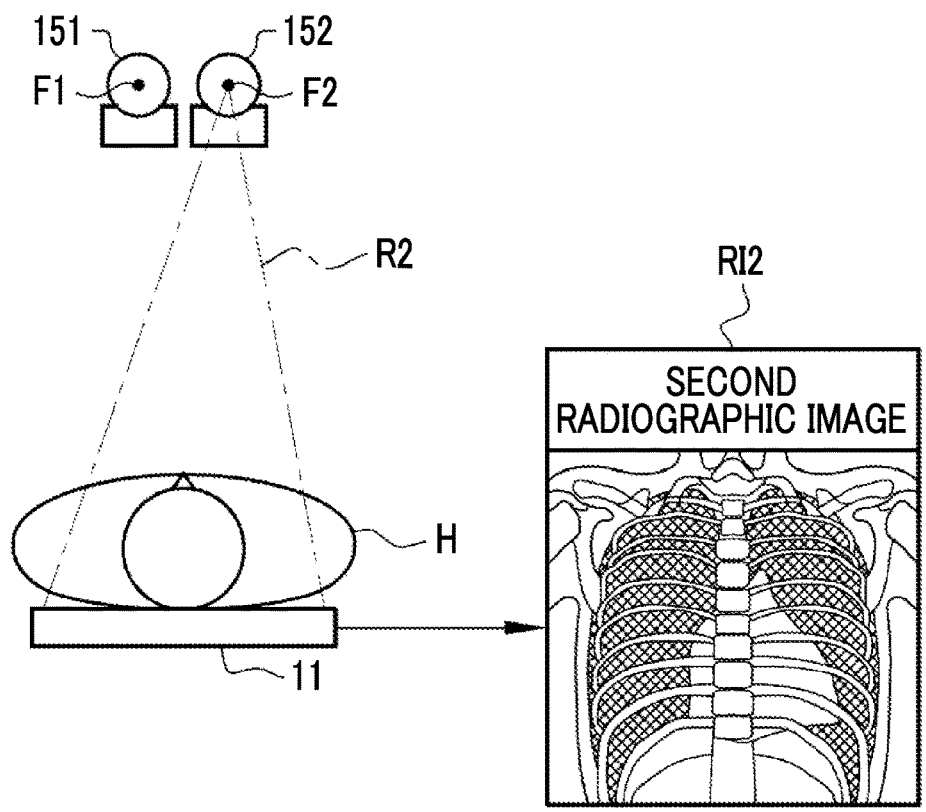
FIG. 6 is a diagram illustrating an aspect in which a second radiation tube generates the second radiation and the radiation detector outputs a second radiographic image based on the second radiation transmitted through the subject.

FIG. 5 illustrates an aspect in which the first radiation tube 151 generates the first radiation R1 and the radiation detector 11 outputs a first radiographic image RI1 based on the first radiation R1 transmitted through the subject H. In contrast, FIG. 6 illustrates an aspect in which the second radiation tube 152 generates the second radiation R2 and the radiation detector 11 outputs a second radiographic image RI2 based on the second radiation R2 transmitted through the subject H. As such, the radiography apparatus 2 can perform ES imaging in which the radiation source 10 continuously emits the first radiation R1 and the second radiation R2 having different energy distributions ED as illustrated in FIG. 4 and the radiation detector 11 outputs the first radiographic image RI1 and the second radiographic image RI2.

The first radiographic image RI1 and the second radiographic image RI2 include both bone tissues, such as the ribs and the spine, and soft tissues, such as the lung and the stomach. However, the energy levels of the radiation R that are easily absorbed by the bone tissues and the soft tissues are different from each other. Therefore, the bone tissue included in the first radiographic image RI1 and the bone tissue included in the second radiographic image RI2 have different pixel values. In addition, the soft tissue included in the first radiographic image RI1 and the soft tissue included in the second radiographic image RI2 have different pixel values.

Figure 7:
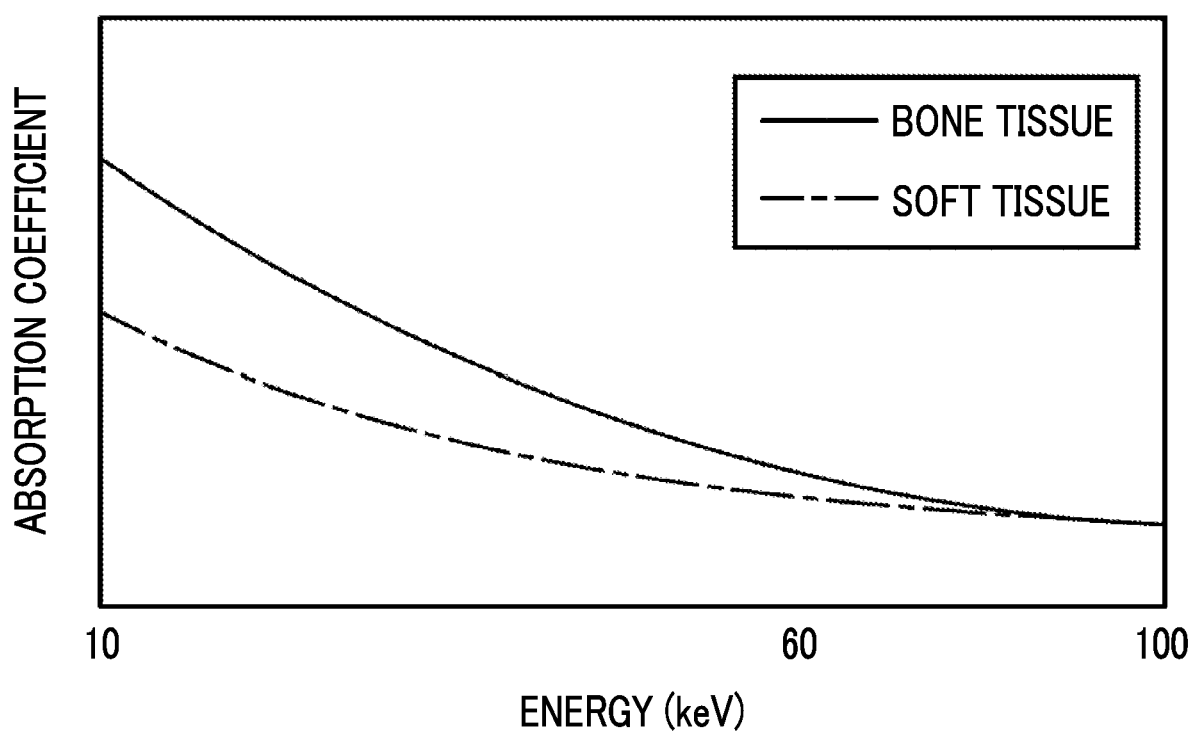
FIG. 7 is a graph illustrating absorption coefficients of a bone tissue and a soft tissue for the energy of radiation.

Specifically, as illustrated in FIG. 7, the difference between an absorption coefficient of the bone tissue and an absorption coefficient of the soft tissue for the radiation R with relatively high energy is small. On the other hand, the difference between an absorption coefficient of the bone tissue and an absorption coefficient of the soft tissue for the radiation R with relatively low energy is large. The radiation R with relatively high energy is the first radiation R1 and the radiation R with relatively low energy is the second radiation R2. Therefore, in the first radiographic image RI1, the ratio of the pixel value of the bone tissue to the pixel value of the soft tissue is low. In contrast, in the second radiographic image RI2, the ratio of the pixel value of the bone tissue to the pixel value of the soft tissue is high.

Figure 8:
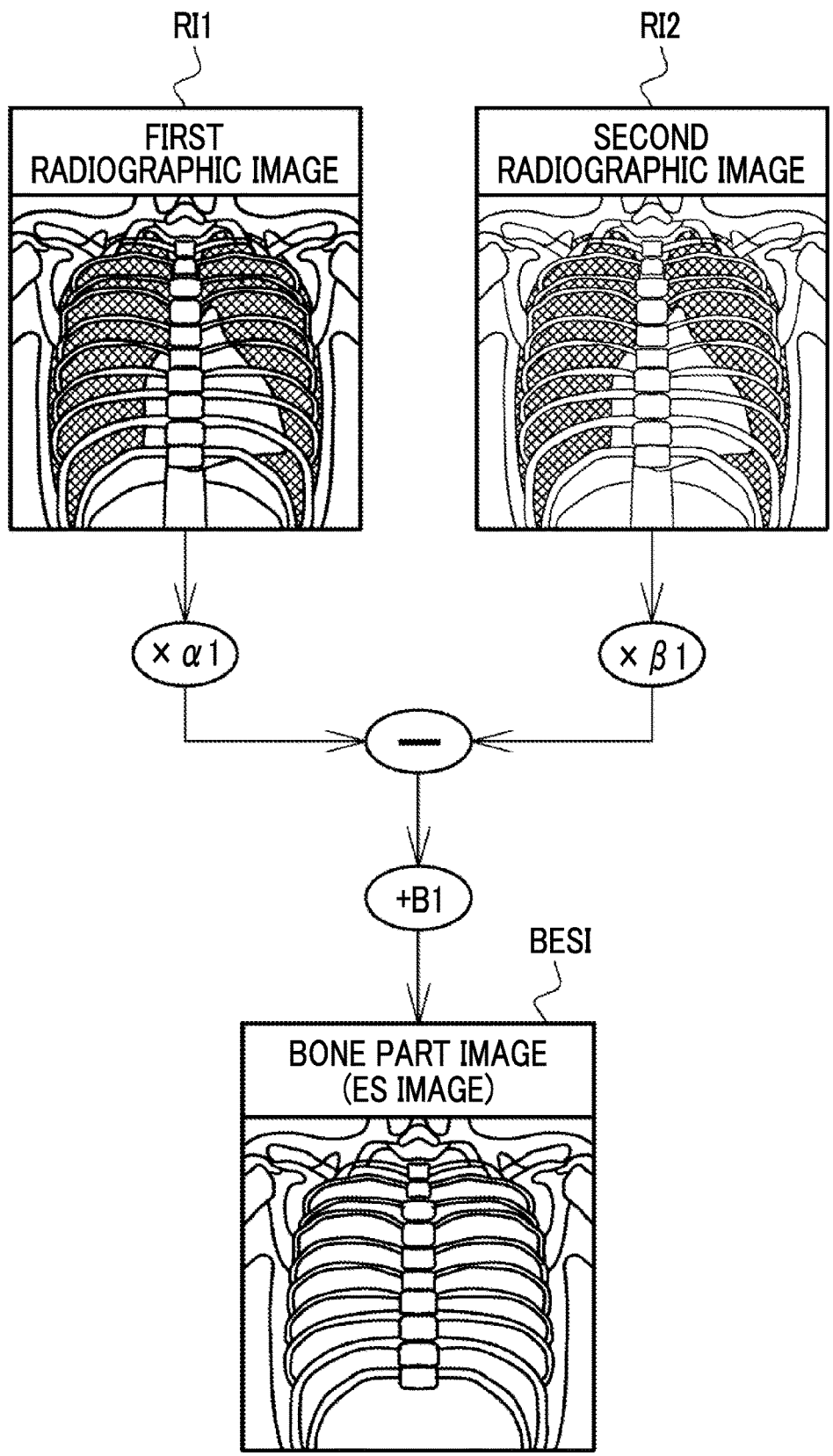
FIG. 8 is a diagram illustrating an aspect in which a bone part image is generated.
Figure 9:
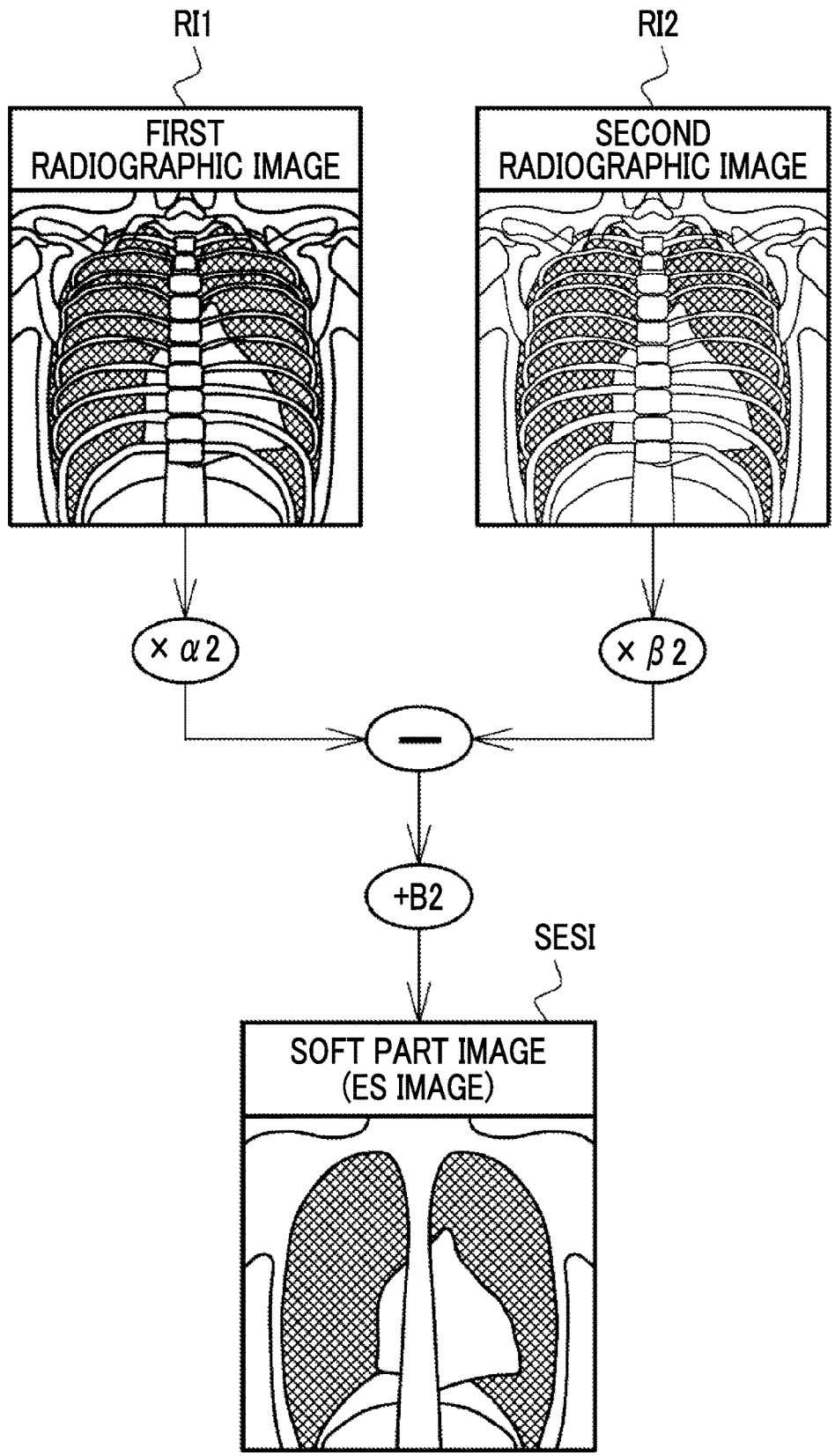
FIG. 9 is a diagram illustrating an aspect in which a soft part image is generated.

FIGS. 8 and 9 illustrate aspects in which an ES image in which a structure in the subject H has been highlighted is generated on the basis of the first radiographic image RI1 and the second radiographic image RI2, using the difference between the absorption coefficients of the bone tissue and the soft tissue for the radiation R illustrated in FIG. 7. FIG. 8 illustrates an aspect in which a bone part image BESI in which the bone tissue has been highlighted is generated. In contrast, FIG. 9 illustrates an aspect in which a soft part image SESI in which the soft tissue has been highlighted is generated. Hereinafter, in some cases, the bone part image BESI and the soft part image SESI are collectively referred to as an "ES image ESI".

In FIG. 8, the bone part image BESI is generated by performing calculation represented by the following Expression (1):

$$BESI = RI1 \times \alpha 1 - RI2 \times \beta 1 + B1 \qquad (1).$$

In addition, $\alpha 1$ and $\beta 1$ are weighting coefficients and B1 is a bias value.

The weighting coefficients $\alpha 1$ and $\beta 1$ are adjusted to values at which the pixel values of the soft tissues in the first radiographic image RI1 and the second radiographic image RI2 are matched with each other. Therefore, in a case in which the pixel value of the first radiographic image RI1 is multiplied by the weighting coefficient $\alpha 1$ and the pixel value of the second radiographic image RI2 is multiplied by the weighting coefficient $\beta 1$ and the difference between the pixel values is calculated, it is possible to generate the bone part image BESI in which the soft tissues have been removed and only the bone tissues have been drawn.

In FIG. 9, the soft part image SESI is generated by performing calculation represented by the following Expression (2):

$$SESI = RI1 \times \alpha 2 - RI2 \times \beta 2 + B2 \qquad (2).$$

In addition, $\alpha 2$ and $\beta 2$ are weighting coefficient and B2 is a bias value.

Similarly to the weighting coefficients $\alpha 1$ and $\beta 1$, the weighting coefficients $\alpha 2$ and $\beta 2$ are adjusted to values at which the pixel values of the bone tissues in the first radiographic image RI1 and the second radiographic image RI2 are matched with each other. Therefore, in a case in which the pixel value of the first radiographic image RI1 is multiplied by the weighting coefficient $\alpha 2$ and the pixel value of the second radiographic image RI2 is multiplied by the weighting coefficient $\beta 2$ and the difference between the pixel values is calculated, it is possible to generate the soft part image SESI in which the bone tissues have been removed and only the soft tissues have been drawn.

Figure 10:
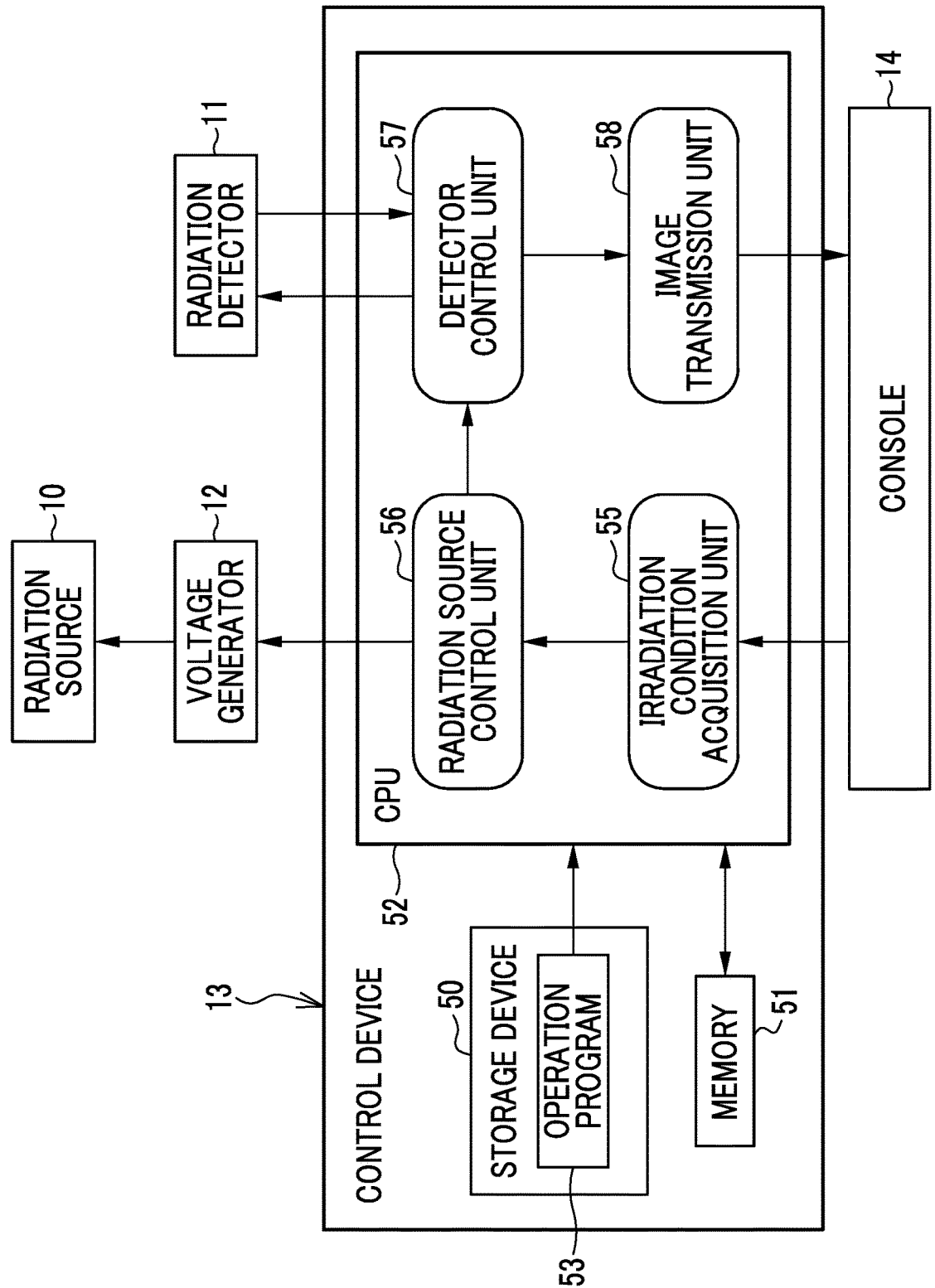
FIG. 10 is a block diagram illustrating a CPU of a control device.

As illustrated in FIG. 10, the control device 13 comprises a storage device 50, a memory 51, and a central processing unit (CPU) 52. The storage device 50 is, for example, a hard disk drive. The storage device 50 stores an operation program 53. The operation program 53 is an example of a "radiography apparatus operation program" according to the technology of the present disclosure. In a case in which the operation program 53 is started, the CPU 52 functions as an irradiation condition acquisition unit 55, a radiation source control unit 56, a detector control unit 57, and an image transmission unit 58 in cooperation with, for example, a memory (not illustrated). The storage device 50, the memory 51, and the CPU 52 are an example of a "computer" according to the technology of the present disclosure.

The irradiation condition acquisition unit 55 acquires the irradiation conditions transmitted from the console 14. The irradiation condition acquisition unit 55 outputs the acquired irradiation conditions to the radiation source control unit 56.

The radiation source control unit 56 controls the operation of the radiation source 10. The radiation source control unit 56 sets the irradiation conditions from the irradiation condition acquisition unit 55 in the voltage generator 12. In a case in which a radiography start command is input, the radiation source control unit 56 directs the radiation tube 15 to generate the radiation R under the set irradiation conditions. The radiation source control unit 56 outputs an irradiation start notification signal for notifying the start of the emission of the radiation R and an irradiation end notification signal for notifying the end of the emission of the radiation R to the detector control unit 57. In addition, as illustrated in FIGS. 5 and 6, the radiation source control unit 56 performs control to direct the radiation source 10 to emit the first radiation R1 and the second radiation R2 in order to acquire the ES image ESI.

The detector control unit 57 controls the operation of the radiation detector 11. The detector control unit 57 directs the radiation detector 11 to perform the accumulation operation in response to the irradiation start notification signal from the radiation source control unit 56. In addition, the detector control unit 57 directs the radiation detector 11 to perform the reading operation in response to the irradiation end notification signal from the radiation source control unit 56. Then, the detector control unit 57 directs the radiation detector 11 to output the radiographic image RI. The detector control unit 57 receives the radiographic image RI transmitted from the radiation detector 11 and outputs the received radiographic image RI to the image transmission unit 58. Further, as illustrated in FIGS. 5 and 6, the detector control unit 57 performs control to direct the radiation detector 11 to output the first radiographic image RI1 based on the first radiation R1 and the second radiographic image RI2 based on the second radiation R2.

The image transmission unit 58 transmits the radiographic image RI from the detector control unit 57 to the console 14.

Figure 11:
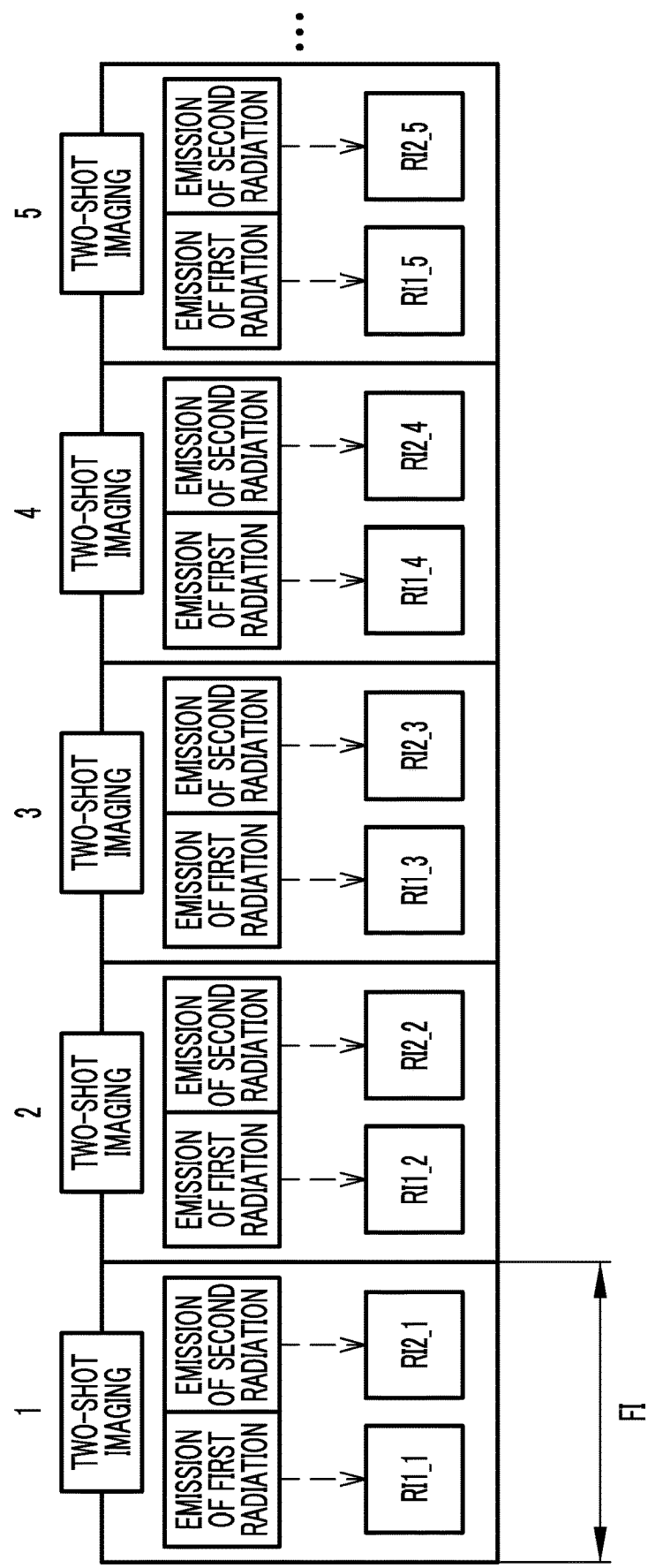
FIG. 11 is a diagram illustrating a moving image capture mode.

The radiography apparatus 2 performs a moving image capture mode that continuously acquires a plurality of radiographic images RI required for displaying a moving image according to a preset frame interval FI. In a case in which the moving image capture mode is performed, the radiation source control unit 56 and the detector control unit 57 perform a two-shot imaging operation in each of frames 1, 2, 3, . . . . Specifically, as illustrated in FIG. 11, the radiation source control unit 56 performs control to direct the radiation source 10 to continuously emit the first radiation R1 and the second radiation R2 in each of frames 1, 2, 3, . . . . In addition, the detector control unit 57 performs control to direct the radiation detector 11 to output the first radiographic image RI1 based on the first radiation R1 and the second radiographic image RI2 based on the second radiation R2 in each of frames 1, 2, 3, . . . . That is, the two-shot imaging operation indicates radiography in which the first radiation R1 and the second radiation R2 are continuously emitted and the radiation detector 11 outputs the first radiographic image RI1 and the second radiographic image RI2. The frame interval FI is, for example, about 0.03 seconds (30 frames/second in frame rate).

Figure 12:
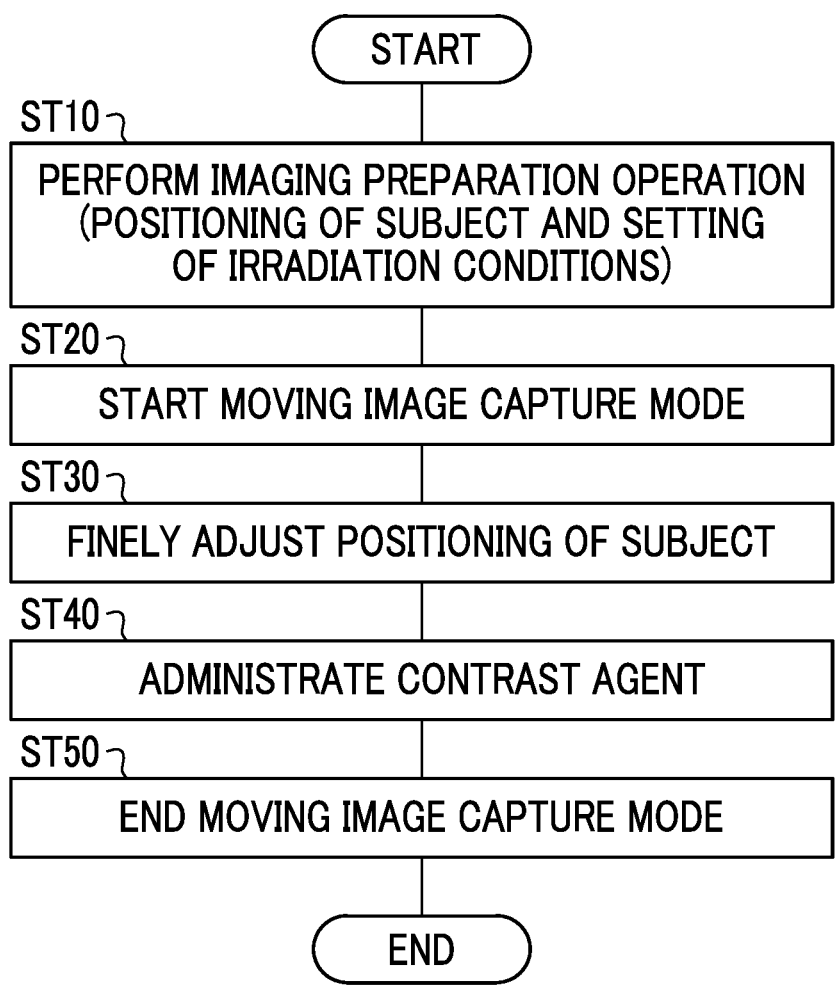
FIG. 12 is a diagram illustrating an imaging procedure in the case of the moving image capture mode.

As illustrated in FIG. 12, in the case of the moving image capture mode, an imaging procedure is started from an imaging preparation operation (Step ST10). The imaging preparation operation includes, specifically, an operation of positioning the subject H in the radiography room and an operation of inputting irradiation conditions to the console 14 in the control room. In the case of the moving image capture mode, as the irradiation conditions, the tube voltage, tube current, and irradiation time of each of the first radiation R1 and second radiation R2 are set. The irradiation time is the time required to emit the first radiation R1 once and the time required to emit the second radiation R2 once.

After the imaging preparation operation ends, the operator operates the irradiation switch 17 to input a command to start the moving image capture mode to the radiography apparatus 2 in the control room (Step ST20).

The operator instructs the subject H to finely adjust the positioning of the subject H while viewing the radiographic image RI (see FIG. 16) displayed on a display 64 of the console 14 in the control room (Step ST30) and instructs the administration of a contrast agent to the subject H (Step ST40). In a case in which it is determined that desired imaging has been performed, the operator stops the operation of the irradiation switch 17 to end the moving image capture mode (Step ST50).

Figure 13:
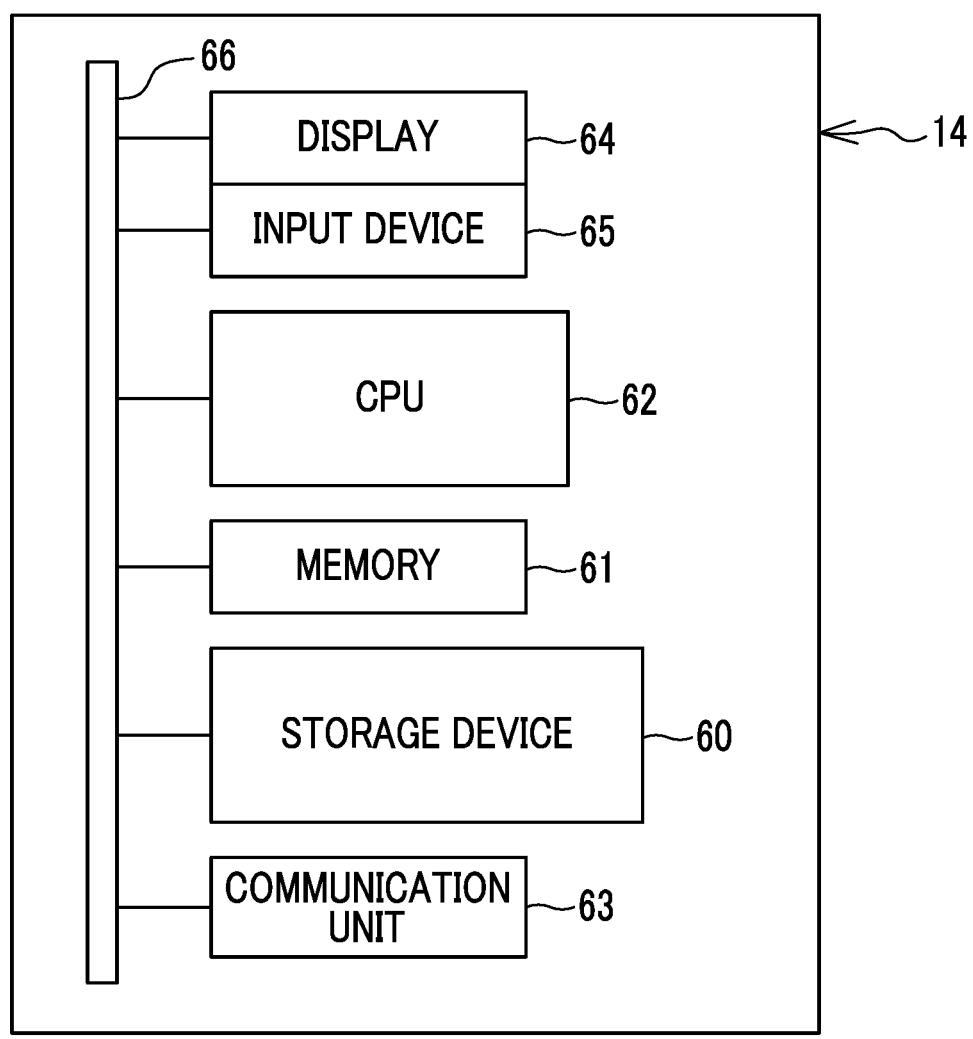
FIG. 13 is a block diagram illustrating a computer forming a console.

In FIG. 13, a computer forming the console 14 comprises a storage device 60, a memory 61, a central processing unit (CPU) 62, a communication unit 63, the display 64, and an input device 65. These units are connected to each other through a bus line 66.

The storage device 60 is a hard disk drive that is provided in the computer forming the console 14 or is connected through a cable of a network. Alternatively, the storage device 60 is a disk array configured by connecting a plurality of hard disk drives. The storage device 60 stores a control program, such as an operating system, various application programs, and various kinds of data associated with these programs.

The memory 61 is a work memory used by the CPU 62 to perform processes. The CPU 62 loads the program stored in the storage device 60 to the memory 61 and performs processes according to the program to control the overall operation of each unit of the computer.

The communication unit 63 is a network interface that controls the transmission of various kinds of information through, for example, the network 20. The display 64 displays various screens. The computer forming the console 14 receives an operation command input from the input device 65 through various screens. The input device 65 includes, for example, a keyboard, a mouse, and a touch panel.

Figure 14:
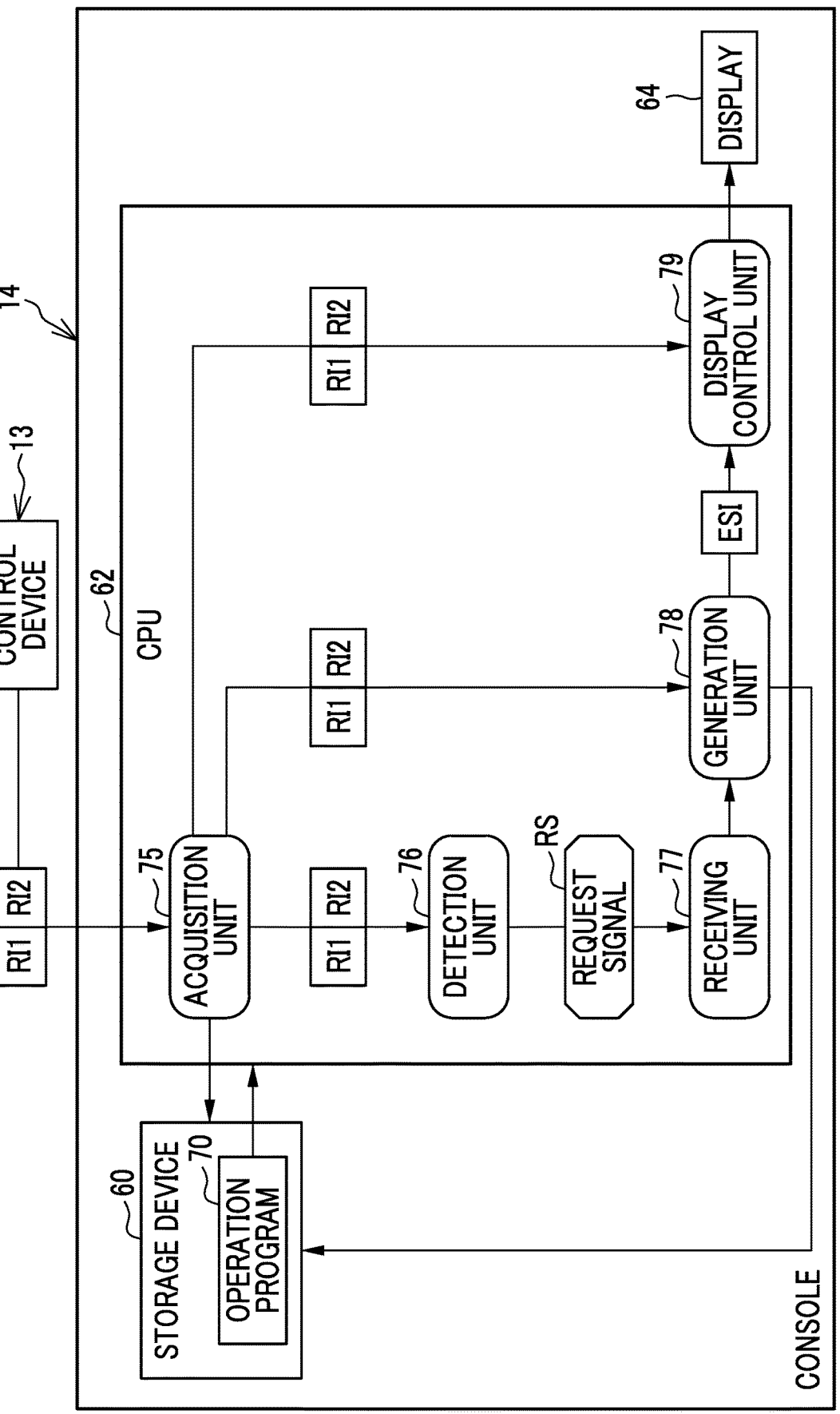
FIG. 14 is a block diagram illustrating a CPU of the console.

In FIG. 14, an operation program 70 is stored in the storage device 60 of the console 14. The operation program 70 is an application program that causes the computer to function as the console 14. That is, the operation program 70 is an example of a "radiography apparatus operation program" according to the technology of the present disclosure.

In a case in which the operation program 70 is started, the CPU 62 of the computer forming the console 14 functions as an acquisition unit 75, a detection unit 76, a receiving unit 77, a generation unit 78, and a display control unit 79 in cooperation with the memory 61.

The acquisition unit 75 acquires the first radiographic image RI1 and the second radiographic image RI2 transmitted from the control device 13 for each two-shot imaging operation. The acquisition unit 75 outputs the first radiographic image RI1 and the second radiographic image RI2 to the detection unit 76, the generation unit 78, and the display control unit 79. In addition, the acquisition unit 75 stores the first radiographic image RI1 and the second radiographic image RI2 in the storage device 60.

The detection unit 76 detects whether or not a contrast agent 16 has been administered to the subject H. For example, the detection unit 76 calculates the differences between the values of pixels of the first radiographic image RI1 and the second radiographic image RI2. The detection unit 76 detects that the contrast agent 16 has been administered to the subject H in a case in which an average value of the absolute values of the differences is equal to or greater than a threshold value. In a case in which it is detected that the contrast agent 16 has been administered to the subject H, the detection unit 76 outputs a request signal RS requesting the generation of an ES image ESI to be referred to for diagnosis to the receiving unit 77. After a predetermined period PD (see FIG. 15) elapses, the detection unit 76 stops the output of the request signal RS.

The receiving unit 77 receives the request signal RS from the detection unit 76. The receiving unit 77 outputs a signal indicating whether or not the request signal RS has been received to the generation unit 78.

The generation unit 78 generates the ES image ESI on the basis of the first radiographic image RI1 and the second radiographic image RI2 from the acquisition unit 75 as illustrated in FIGS. 8 and 9. The generation unit 78 outputs the ES image ESI to the display control unit 79. In addition, the generation unit 78 stores the generated ES image ESI in the storage device 60.

The display control unit 79 performs control to display various screens on the display 64. For example, the display control unit 79 performs control to display an image display screen 85 (see FIG. 16) on the display 64.

Figure 15:
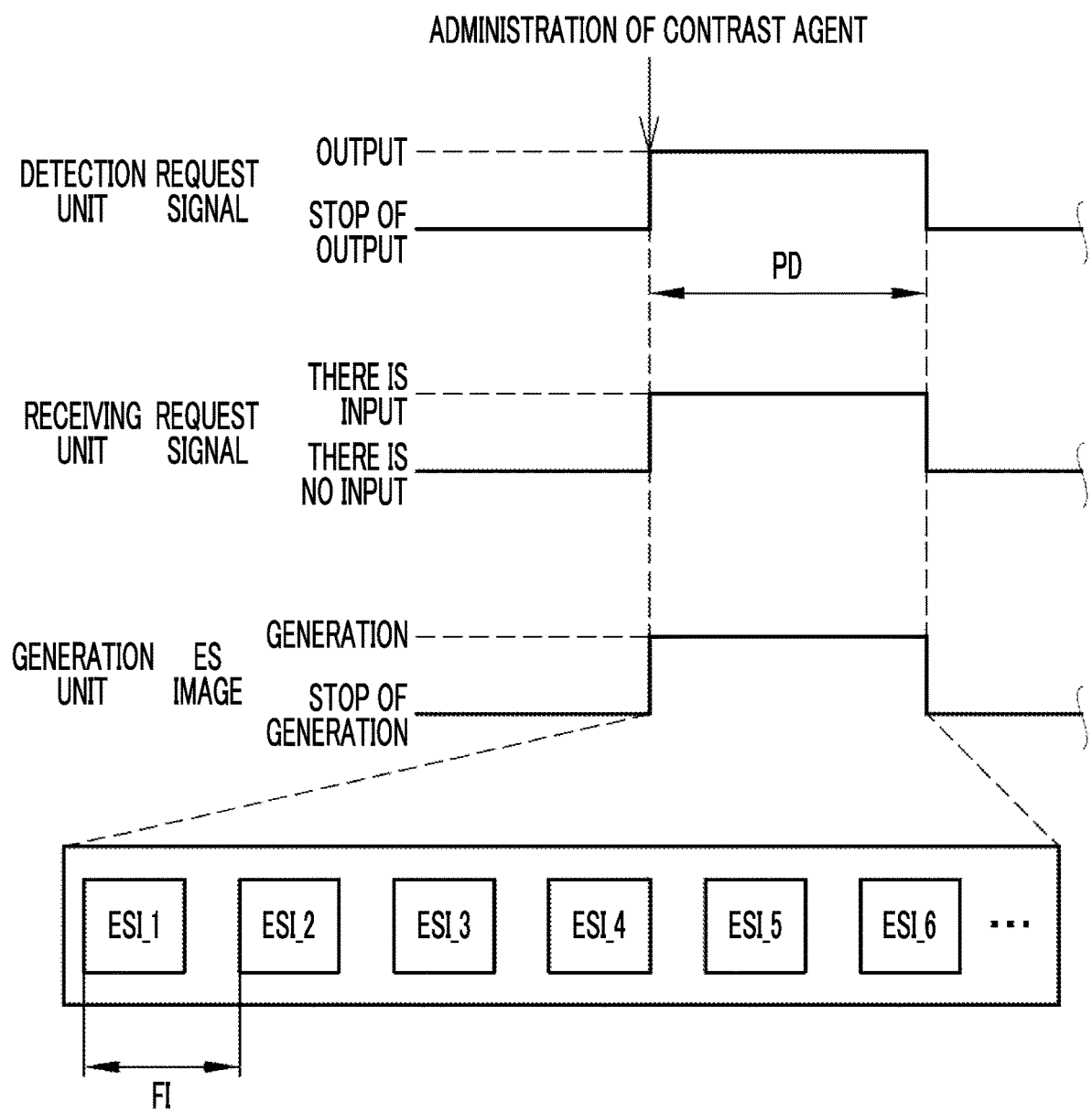
FIG. 15 is a timing chart illustrating a detection unit, a receiving unit, and a generation unit.

As illustrated in FIG. 15, the generation unit 78 does not generate the ES image ESI in a case in which the receiving unit 77 does not receive the request signal RS during the moving image capture mode. The case in which the receiving unit 77 does not receive the request signal RS is a case in which the detection unit 76 does not detect that the contrast agent 16 has been administered to the subject H. In addition, the case in which the receiving unit 77 does not receive the request signal RS is a case in which the period PD has elapsed since the detection unit 76 had detected the administration of the contrast agent 16 to the subject H.

In contrast, the generation unit 78 generates the ES image ESI in a case in which the receiving unit 77 receives the request signal RS during the moving image capture mode. The receiving unit 77 receives the request signal RS until the period PD elapses since the detection unit 76 has detected the administration of the contrast agent 16 to the subject H. The generation unit 78 generates the ES image ESI at a preset frame interval FI. The period PD is, for example, 5 seconds.

Figure 16:
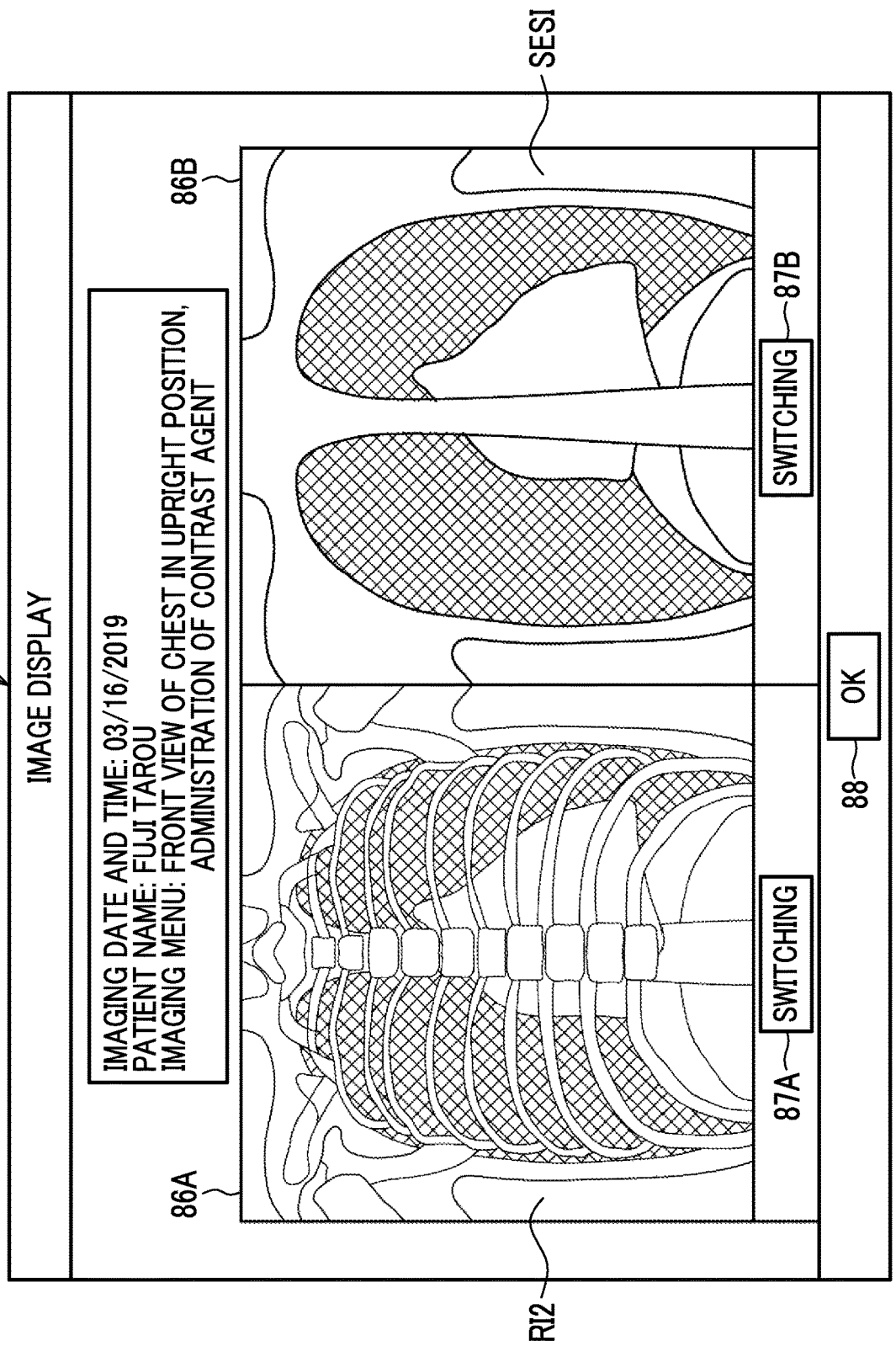
FIG. 16 is a diagram illustrating an image display screen.

As illustrated in FIG. 16, a first display frame 86A and a second display frame 86B are provided in the image display screen 85 displayed on the display 64 under the control of the display control unit 79. One of the first radiographic image RI1 and the second radiographic image RI2 is displayed in the first display frame 86A. The ES image ESI, that is, one of the bone part image BESI and the soft part image SESI is displayed in the second display frame 86B. In a case in which the generation unit 78 does not generate the ES image ESI, no images are displayed in the second display frame 86B. FIG. 16 illustrates a state in which the second radiographic image RI2 is displayed in the first display frame 86A and the soft part image SESI is displayed in the second display frame 86B.

A first switching button 87A is provided below the first display frame 86A and a second switching button 87B is provided below the second display frame 86B. In a case in which the first switching button 87A is selected, the display control unit 79 switches the display of the first radiographic image RI1 and the second radiographic image RI2 in the first display frame 86A. In a case in which the second switching button 87B is selected, the display control unit 79 switches the display of the bone part image BESI and the soft part image SESI in the second display frame 86B. In a case in which an OK button 88 is selected, the display control unit 79 turns off the display of the image display screen 85.

Next, the operation of the above-mentioned configuration will be described with reference to flowcharts illustrated in FIGS. 17 to 19. In a case in which the operation program 53 is started in the control device 13, the CPU 52 of the control device 13 functions as the irradiation condition acquisition unit 55, the radiation source control unit 56, the detector control unit 57, and the image transmission unit 58 as illustrated in FIG. 10. In addition, in a case in which the operation program 70 is started in the console 14, the CPU 62 of the console 14 functions as the acquisition unit 75, the detection unit 76, the receiving unit 77, the generation unit 78, and the display control unit 79 as illustrated in FIG. 14.

As illustrated in Step ST10 of FIG. 12, the irradiation conditions set in the console 14 in the imaging preparation operation are acquired by the irradiation condition acquisition unit 55 of the control device 13. The irradiation conditions are output from the irradiation condition acquisition unit 55 to the radiation source control unit 56 and are set in the voltage generator 12 by the radiation source control unit 56.

Figure 17:
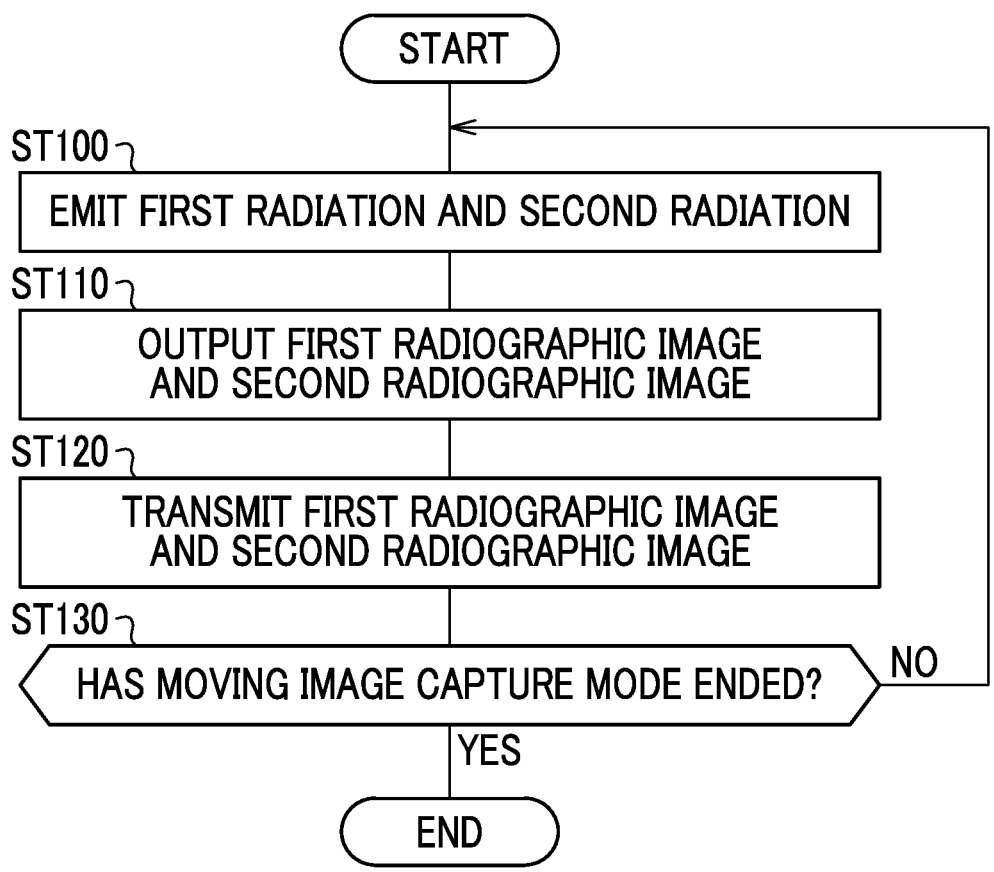
FIG. 17 is a flowchart illustrating a process procedure of the control device.

In FIG. 17, in a case in which the irradiation switch 17 is operated to input a command to start the moving image capture mode, the two-shot imaging operation illustrated in FIG. 11 is performed. Specifically, the radiation source control unit 56 directs the radiation source 10 to continuously emit the first radiation R1 and the second radiation R2 (Step ST100). In addition, the detector control unit 57 directs the radiation detector 11 to output the first radiographic image RI1 and the second radiographic image RI2 (Step ST110). Step ST100 is an example of a "radiation source control step" according to the technology of the present disclosure. Step ST110 is an example of a "detector control step" according to the technology of the present disclosure.

The first radiographic image RI1 and the second radiographic image RI2 are output from the detector control unit 57 to the image transmission unit 58. The first radiographic image RI1 and the second radiographic image RI2 are transmitted to the console 14 by the image transmission unit 58 (Step ST120). In the control device 13, the process from Step ST100 to Step ST120 is repeatedly performed until the moving image capture mode ends (YES in Step ST130).

Figure 18:
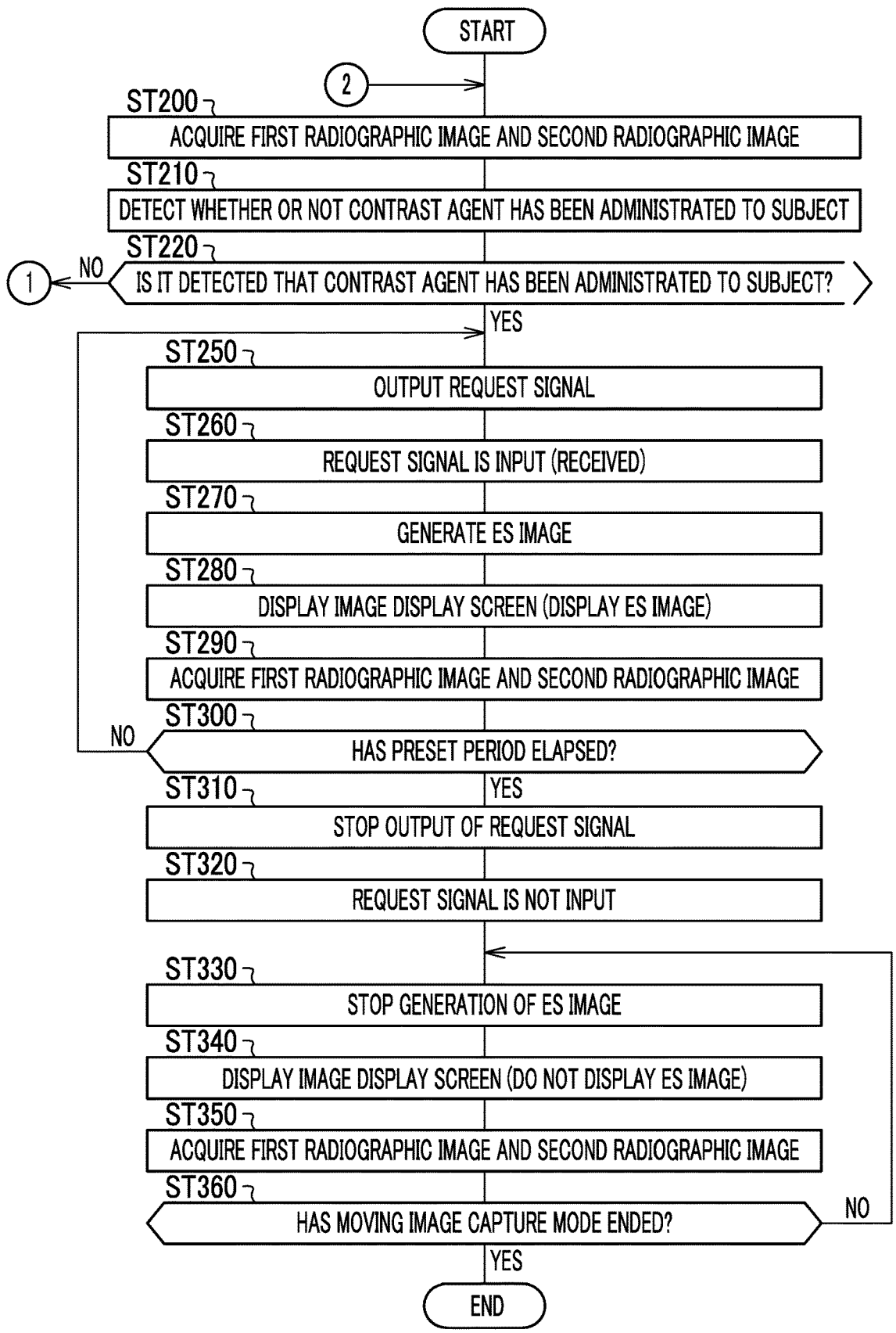
FIG. 18 is a flowchart illustrating a process procedure of the console.
Figure 19:
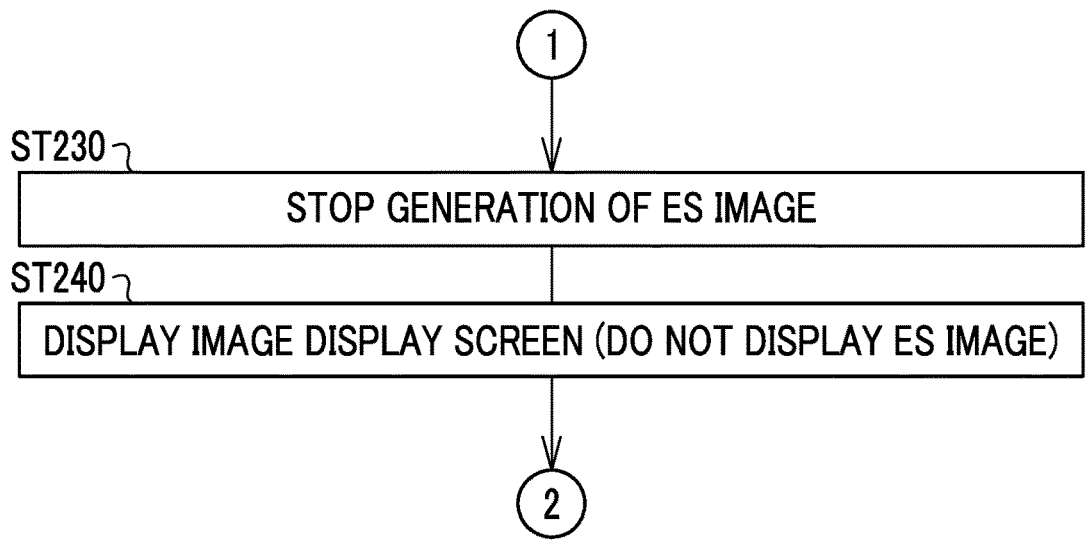
FIG. 19 is a flowchart illustrating a process procedure of the console.

In FIG. 18, in the console 14, the acquisition unit 75 acquires the first radiographic image RI1 and the second radiographic image RI2 from the control device 13 (Step ST200). The first radiographic image RI1 and the second radiographic image RI2 are output from the acquisition unit 75 to the detection unit 76, the generation unit 78, and the display control unit 79. In addition, the first radiographic image RI1 and the second radiographic image RI2 are stored in the storage device 60. Step ST200 is an example of an "acquisition step" according to the technology of the present disclosure.

The detection unit 76 detects whether or not the contrast agent 16 has been administered to the subject H on the basis of the first radiographic image RI1 and the second radiographic image RI2 (Step ST210). In a case in which the detection unit 76 does not detect that the contrast agent 16 has been administered to the subject H (NO in Step ST220), the generation unit 78 does not generate the ES image ESI as illustrated in FIG. 19 (Step ST230). The image display screen 85 is displayed on the display 64 under the control of the display control unit 79 (Step ST240). In this case, the ES image ESI is not displayed in the second display frame 86B. Step ST230 is an example of a "non-generation step" according to the technology of the present disclosure.

On the other hand, in a case in which the detection unit 76 detects that the contrast agent 16 has been administered to the subject H (YES in Step ST220), the detection unit 76 outputs the request signal RS to the receiving unit 77 (Step ST250). Then, the request signal RS is input to the receiving unit 77 and the receiving unit 77 receives the request signal RS (Step ST260). Then, the receiving unit 77 outputs a signal indicating that the request signal RS has been received to the generation unit 78. Step ST260 is an example of a "receiving step" according to the technology of the present disclosure.

In a case in which the receiving unit 77 receives the request signal RS, the generation unit 78 generates the ES image ESI (Step ST270). The ES image ESI is output from the generation unit 78 to the display control unit 79. In addition, the ES image ESI is stored in the storage device 60. Step ST270 is an example of a "generation step" according to the technology of the present disclosure.

The image display screen 85 is displayed on the display 64 under the control of the display control unit 79 (Step ST280). In this case, as illustrated in FIG. 16, the ES image ESI is displayed in the second display frame 86B.

Then, as in Step ST200, the first radiographic image RI1 and the second radiographic image RI2 are acquired by the acquisition unit 75 (Step ST290) and are output to the detection unit 76, the generation unit 78, and the display control unit 79. The process from Step ST250 to Step ST290 is repeatedly performed until the preset period PD elapses since the detection unit 76 has detected the administration of the contrast agent 16 to the subject H (YES in Step ST300). Step ST290 is also an example of the "acquisition step" according to the technology of the present disclosure.

After the period PD elapses since the detection of the administration of the contrast agent 16 to the subject H (YES in Step ST300), the output of the request signal RS from the detection unit 76 is stopped (Step ST310). Then, the request signal RS is not input to the receiving unit 77 and the receiving unit 77 does not receive the request signal RS (Step ST320). As in Step ST230, the generation unit 78 does not generate the ES image ESI (Step ST330). As in Step ST240, the image display screen 85 on which the ES image ESI is not displayed is displayed on the display 64 under the control the display control unit 79 (Step ST340). Step ST330 is also an example of the "non-generation step" according to the technology of the present disclosure.

Then, as in Steps ST200 and ST290, the first radiographic image RI1 and the second radiographic image RI2 are acquired by the acquisition unit 75 (Step ST350) and are output to the detection unit 76, the generation unit 78, and the display control unit 79. The process from Step ST330 to Step ST350 is repeatedly performed until the moving image capture mode ends (YES in Step ST360). Step ST350 is also an example of the "acquisition step" according to the technology of the present disclosure.

As described above, the radiation source control unit 56 performs control to direct the radiation source 10 to emit the first radiation R1 and the second radiation R2 in order to perform the moving image capture mode that continuously acquires the radiographic image RI required for the display of a moving image according to the preset frame interval FI. In a case in which the moving image capture mode is performed, the detector control unit 57 performs control to direct the radiation detector 11 to continuously output the first radiographic image RI1 based on the first radiation R1 and the second radiographic image RI2 based on the second radiation R2. The acquisition unit 75 acquires the first radiographic image RI1 and the second radiographic image RI2. The receiving unit 77 receives the request signal RS to request the generation of the ES image ESI referred to for diagnosis. The generation unit 78 generates the ES image ESI on the basis of the first radiographic image RI1 and the second radiographic image RI2 acquired by the acquisition unit 75. As illustrated in FIG. 15, the generation unit 78 does not generate the ES image ESI in a case in which the receiving unit 77 does not receive the request signal RS. In contrast, the generation unit 78 generates the ES image ESI in a case in which the receiving unit 77 receives the request signal RS. Therefore, it is possible to effectively generate the ES image ESI to be referred to for diagnosis. In addition, it is possible to reduce the load on the process of generating the ES image ESI.

The radiography apparatus 2 according to this embodiment comprises the detection unit 76 that detects whether or not the contrast agent 16 has been administered to the subject H and outputs the request signal RS to the receiving unit 77 in a case in which it is detected that the contrast agent 16 has been administered to the subject H. Therefore, it is possible to reliably acquire the ES image ESI which includes an image of the contrast agent 16 and is very likely to be referred to for diagnosis, without a complicated operation of the operator.

A device for administrating the contrast agent 16 to the subject H may be used. In this configuration, in a case in which a signal indicating the administration of the contrast agent 16 to the subject H has been received, it may be detected that the contrast agent 16 has been administered to the subject H.

The radiography apparatus 2 according to this embodiment comprises the display control unit 79 that performs control to display the ES image ESI and at least one of the first radiographic image RI1 or the second radiographic image RI2. Therefore, it is possible to provide the ES image ESI and at least one of the first radiographic image RI1 or the second radiographic image RI2 for the operator's browsing. The operator can input a command to finely adjust the positioning of the subject H illustrated in Step ST30 of FIG. 12 or can check the state of the radiographic image RI.

In a case in which the generation unit 78 does not generate the ES image ESI, at least one of the first radiographic image RI1 or the second radiographic image RI2 may be displayed. In a case in which the generation unit 78 generates the ES image ESI, the ES image ESI may be displayed instead of at least one of the first radiographic image RI1 or the second radiographic image RI2. Further, the first radiographic image RI1, the second radiographic image RI2, the bone part image BESI, and the soft part image SESI may be displayed side by side.

As illustrated in FIGS. 2 and 3, the radiation tube 15 has the cathode 30 which is a cold cathode. The cold cathode generates the amount of heat that is much less than that a cathode with a filament structure which emits thermal electrons. Therefore, a heat radiation structure is not required and it is possible to reduce the size of the radiation tube 15. Specifically, it is possible to reduce the diameter of the radiation tube 15 to, for example, about 50 mm or less. Therefore, this configuration can contribute to reducing the size of the radiation source 10.

In a case in which two radiation tubes 15, that is, the first radiation tube 151 and the second radiation tube 152 are used as in this embodiment and the two radiation tubes 15 have the cathodes 30 which are cold cathodes, the first radiation tube 151 and the second radiation tube 152 can be arranged close to each other since they are small. In other words, it is possible to reduce the distance between the first focus F1 of the first radiation R1 and the second focus F2 of the second radiation R2. Therefore, the deviation of the irradiation angles of the first radiation R1 and the second radiation R2 with respect to the imaging surface of the radiation detector 11 which affects the quality of the ES image ESI is reduced. As a result, it is possible to acquire the ES image ESI having substantially the same quality as that in a case in which one radiation tube 15 is used.

In addition, as illustrated in FIGS. 2 and 3, the cathode 30 is a field emission type having an electron emission source that emits electron beams using the field emission phenomenon. The cathode 30 of the field emission type can generate the radiation R at a shorter interval than the cathode with a filament structure which emits thermal electrons. Therefore, it is possible to increase the number of ES images ESI acquired per unit time.

In this embodiment, two radiation tubes 15, that is, the first radiation tube 151 generating the first radiation R1 and the second radiation tube 152 generating the second radiation R2 are used. Therefore, it is possible to reduce the load applied to the radiation tubes 15, as compared to a case in which one radiation tube 15 is used. In addition, since the emission interval between the first radiation R1 and the second radiation R2 in the two-shot imaging operation is reduced to the limit, it is possible to almost eliminate the influence of the body motion of the subject H from the first radiographic image RI1 and the second radiographic image RI2.

The number of radiation tubes 15 may be 2 or more or may be 1. Even in a case in which one radiation tube 15 is used, the emission interval between the first radiation R1 and the second radiation R2 in the two-shot imaging operation is reduced by using the cathode 30 of the field emission type. Therefore, it is possible to eliminate the influence of the body motion of the subject H from the first radiographic image RI1 and the second radiographic image RI2.

Second Embodiment

Figure 20:
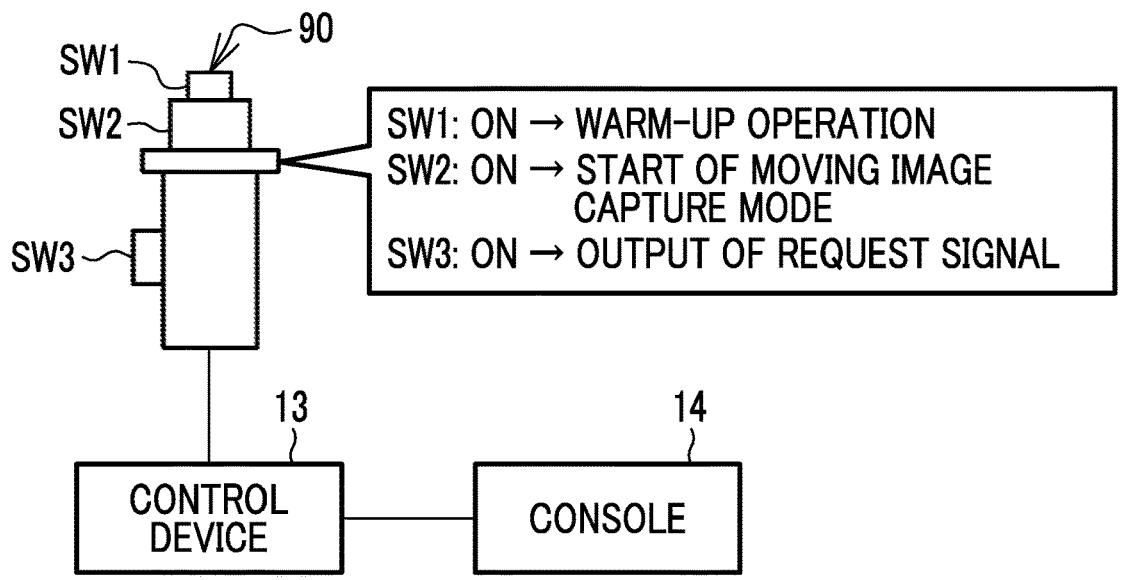
FIG. 20 is a diagram illustrating an irradiation switch that outputs a request signal to the receiving unit in response to an operation command from an operator.
Figure 21:
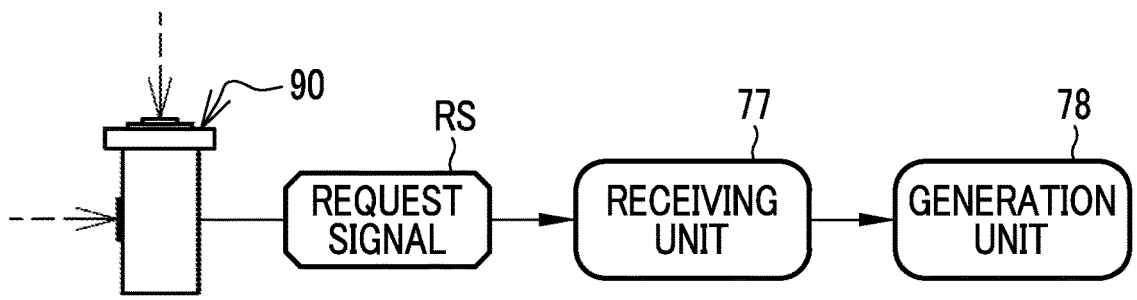
FIG. 21 is a diagram illustrating an aspect in which the receiving unit receives the request signal from the irradiation switch.
Figure 22:
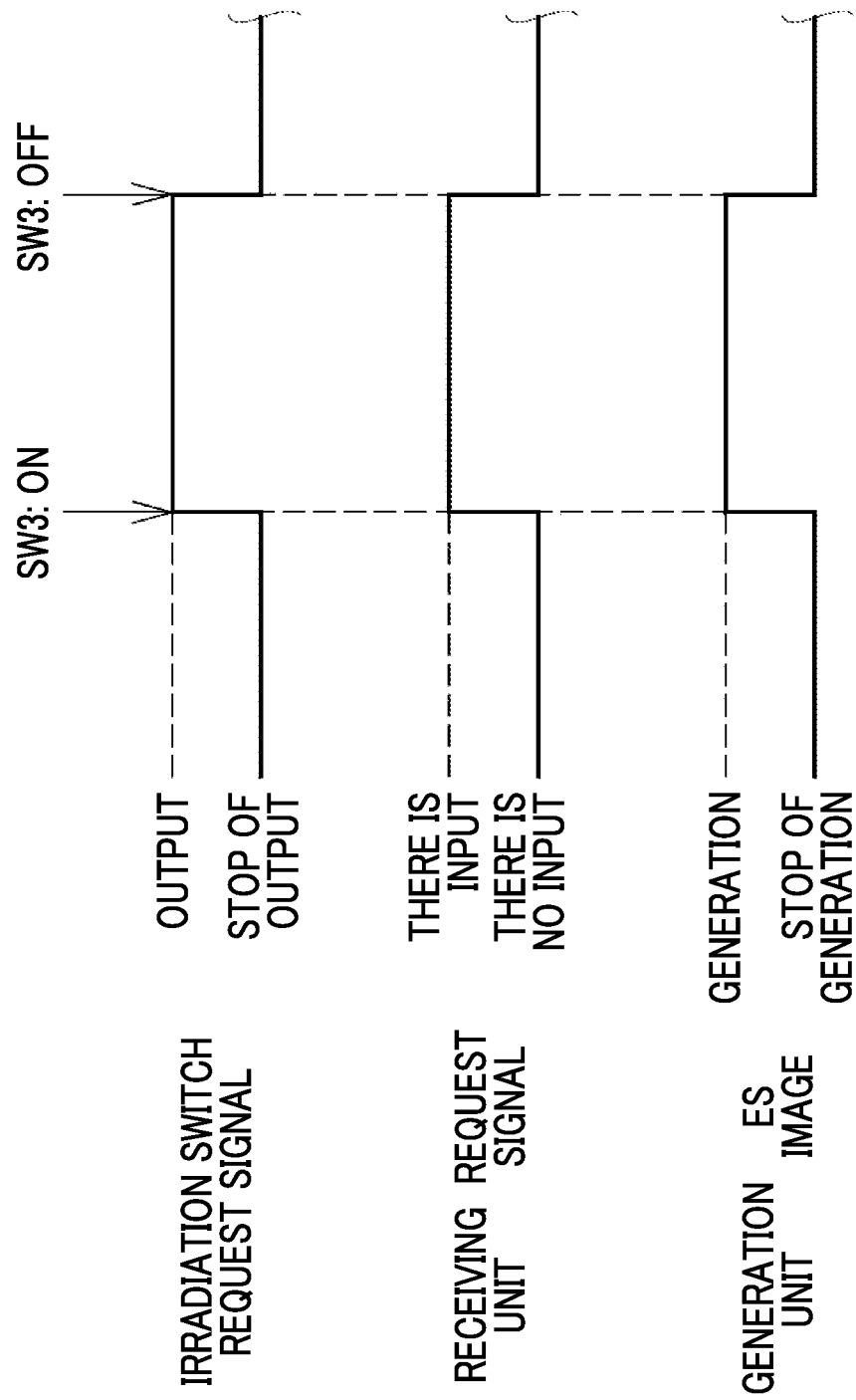
FIG. 22 is a timing chart illustrating a detection unit, a receiving unit, and a generation unit in a second embodiment.

In a Second Embodiment Illustrated in FIGS. 20 to 22, an Operation Unit is Provided which outputs the request signal RS to the receiving unit 77 in response to an operation command from the operator.

In FIG. 20, an irradiation switch 90 is connected to the control device 13 and includes a first switch SW1, a second switch SW2, and a third switch SW3 that are manually operated by the operator. The first switch SW1 and the second switch SW2 are two-stage push switches. In a case in which the first switch SW1 is pressed by the operator, the irradiation switch 90 outputs a signal for directing the radiation source 10 to perform a warm-up operation to the control device 13. In a case in which the second switch SW2 is pressed by the operator, the irradiation switch 90 outputs a signal for starting the moving image capture mode to the control device 13. In a case in which the third switch SW3 is pressed by the operator, the irradiation switch 90 outputs the request signal RS to the control device 13. That is, the irradiation switch 90 is an example of an "operation unit" according to the technology of the present disclosure.

The control device 13 transmits the request signal RS to the console 14. As illustrated in FIG. 21, the receiving unit 77 of the console 14 receives the request signal RS which has been output from the irradiation switch 90 and transmitted from the control device 13. The receiving unit 77 outputs a signal indicating that the request signal RS has been received to the generation unit 78.

As illustrated in FIG. 22, the generation unit 78 does not generate the ES image ESI in a case in which the third switch SW3 of the irradiation switch 90 is turned off and the receiving unit 77 does not receive the request signal RS. In contrast, the generation unit 78 generates the ES image ESI in a case in which the third switch SW3 of the irradiation switch 90 is turned on and the receiving unit 77 receives the request signal RS.

As such, in the second embodiment, the irradiation switch 90 is provided which outputs the request signal RS to the receiving unit 77 in response to an operation command from the operator. In a case in which the operator determines to refer to the ES image ESI for diagnosis, the operator turns on the third switch SW3 of the irradiation switch 90. Therefore, it is possible to reliably acquire the ES image ESI determined by the operator to be referred to for diagnosis.

The operation unit is not limited to the exemplified irradiation switch 90. A switch for outputting the request signal RS may be provided separately from the switch for commanding the start of the moving image capture mode. Instead of the switch manually operated by the operator, a foot switch that is operated by the foot of the operator may be used as the operation unit. The foot switch may be pressed in two stages, a first switch may be pressed to output a signal for directing the radiation source 10 to perform the warm-up operation and a signal for starting the moving image capture mode, and a second switch may be pressed to output the request signal RS.

The second embodiment in which the request signal RS is output to the receiving unit 77 in response to an operation command from the operator and the first embodiment in which the request signal RS is output to the receiving unit 77 in a case in which it is detected that the contrast agent 16 has been administered to the subject H may be combined with each other. In this case, even though the operator does not operate the switch for outputting the request signal RS, the request signal RS is output to the receiving unit 77 in a case in which it is detected that the contrast agent 16 has been administered to the subject H. Further, even though it is not detected that the contrast agent 16 has been administered to the subject H, the request signal RS is output to the receiving unit 77 in a case in which the operator operates the switch for outputting the request signal RS.

Third Embodiment

Figure 23:
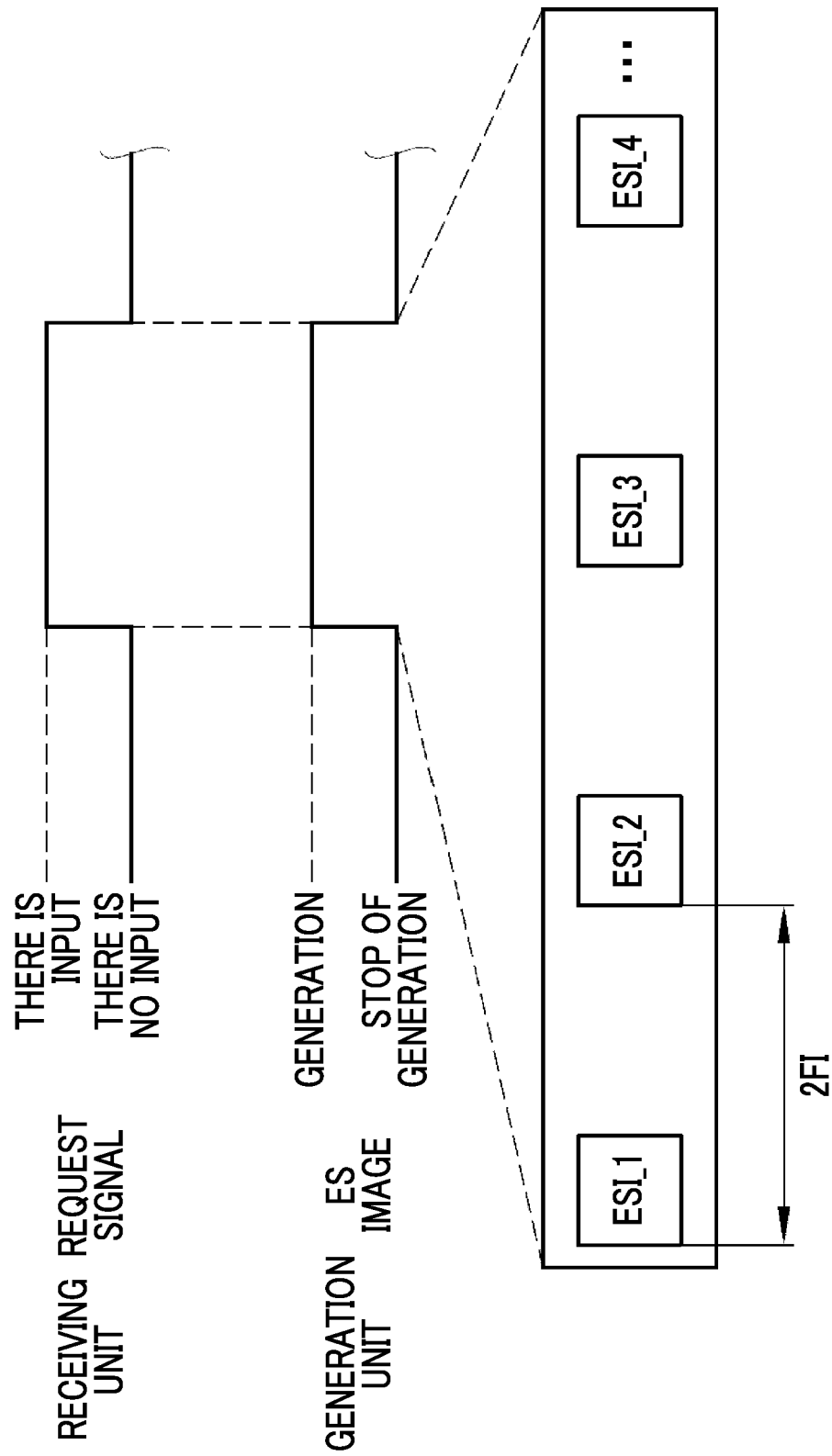
FIG. 23 is a diagram illustrating a third embodiment in which an average value of the generation intervals of an energy subtraction image is greater than a frame interval.
Figure 24:
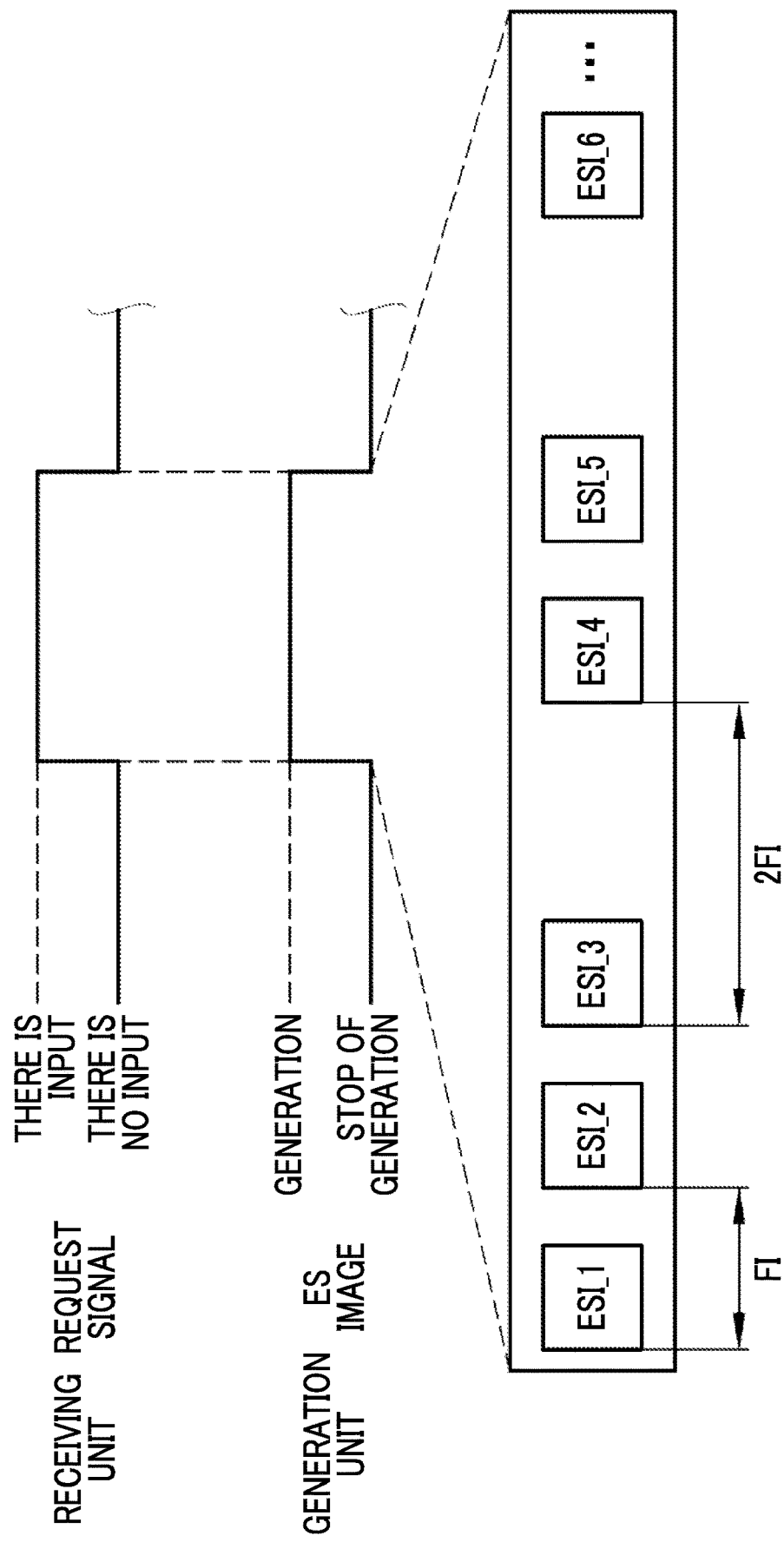
FIG. 24 is a diagram illustrating another example of the third embodiment.

In a third embodiment illustrated in FIGS. 23 and 24, the average value of the generation intervals of the ES image ESI is greater longer than the frame interval FI.

FIG. 23 illustrates an example in which the generation interval of the ES image ESI is 2FI (about 0.07 seconds which is 15 frames/second in frame rate) which is twice the frame interval FI. This configuration in which the average value of the generation intervals of the ES image ESI is greater than the frame interval FI makes is possible to further reduce the load on the process of generating the ES image ESI.

The generation interval of the ES image ESI is not limited to the exemplified 2FI. The generation interval of the ES image ESI may be, for example, 1.5FI, 3FI, or 4FI. Further, as illustrated in FIG. 24, the case in which the ES image ESI is generated at the frame interval FI and the case in which the ES image ESI is generated at an interval longer (here, 2FI is exemplified) than the frame interval FI may be mixed. In the case of FIG. 24, as a result, the average value of the generation intervals of the ES image ESI is greater than the frame interval FI.

Fourth Embodiment

Figure 25:
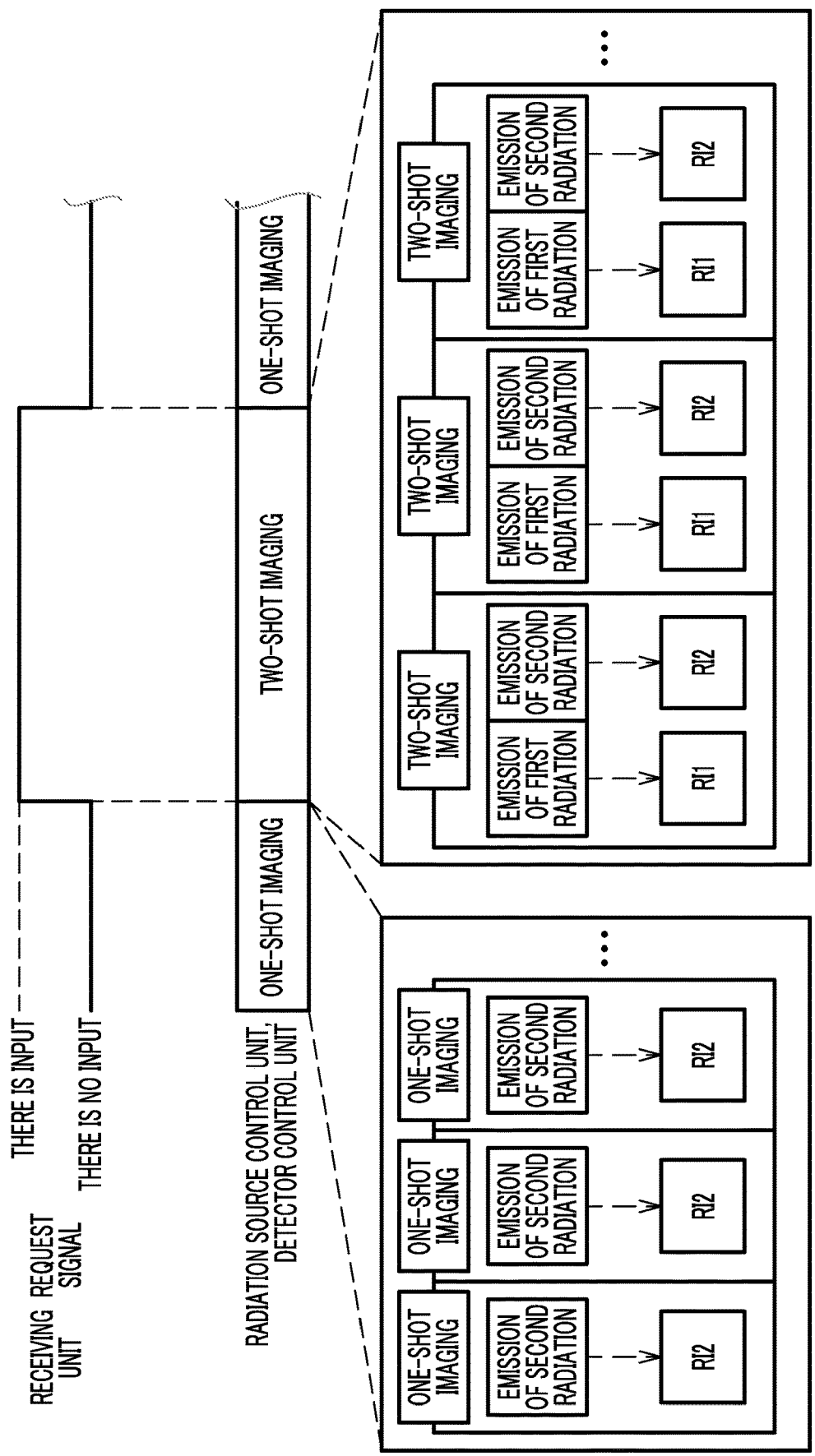
FIG. 25 is a diagram illustrating a fourth embodiment in which a one-shot imaging operation is performed in a case in which the receiving unit does not receive a request signal and a two-shot imaging operation is performed in a case in which the receiving unit receives the request signal.

In FIG. 25, in a moving image capture mode according to a fourth embodiment, the one-shot imaging operation is performed in a case in which the receiving unit 77 does not receive the request signal RS and the two-shot imaging operation is performed in a case in which the receiving unit 77 receives the request signal RS.

In a case in which the first embodiment is applied, the console 14 transmits, to the control device 13, information indicating that the detection unit 76 has output the request signal RS and the receiving unit 77 has received the request signal RS. Then, the radiation source control unit 56 and the detector control unit 57 recognize that the receiving unit 77 has received the request signal RS. In a case in which the second embodiment is applied, the radiation source control unit 56 and the detector control unit 57 directly receive the request signal RS from the operation unit to recognize that the receiving unit 77 has received the request signal RS.

Here, the one-shot imaging operation indicates radiography which directs the radiation source 10 to emit only one of the first radiation R1 and the second radiation R2 and directs the radiation detector 11 to output only one of the first radiographic image RI1 and the second radiographic image RI2. In FIG. 25, only the second radiation R2 is emitted in the one-shot imaging operation. That is, the second radiation R2 is an example of "one of the first radiation and the second radiation" according to the technology of the present disclosure. In this case, in the one-shot imaging operation, the radiation detector 11 outputs only the second radiographic image RI2. That is, the second radiographic image RI2 is an example of "one of the first radiographic image and the second radiographic image" according to the technology of the present disclosure.

In a case in which the receiving unit 77 does not receive the request signal RS, the generation unit 78 does not generate the ES image ESI. Therefore, in a case in which the receiving unit 77 does not receive the request signal RS, the two-shot imaging operation is originally unnecessary. Therefore, in the fourth embodiment, the radiation source control unit 56 and the detector control unit 57 perform the one-shot imaging operation in a case in which the receiving unit 77 does not receive the request signal RS and the two-shot imaging operation is not necessary and perform the two-shot imaging operation only in a case in which the receiving unit 77 receives the request signal RS and the two-shot imaging operation is necessary. This configuration makes it possible to reduce the amount of radiation R. As a result, it is possible to reduce the amount of radiation exposure of the subject H. Further, it is possible to reduce the load applied to the radiation tube 15 and the radiation detector 11 as compared to a case in which the two-shot imaging operation is continuously performed a plurality of times.

Fifth Embodiment

Figure 26:
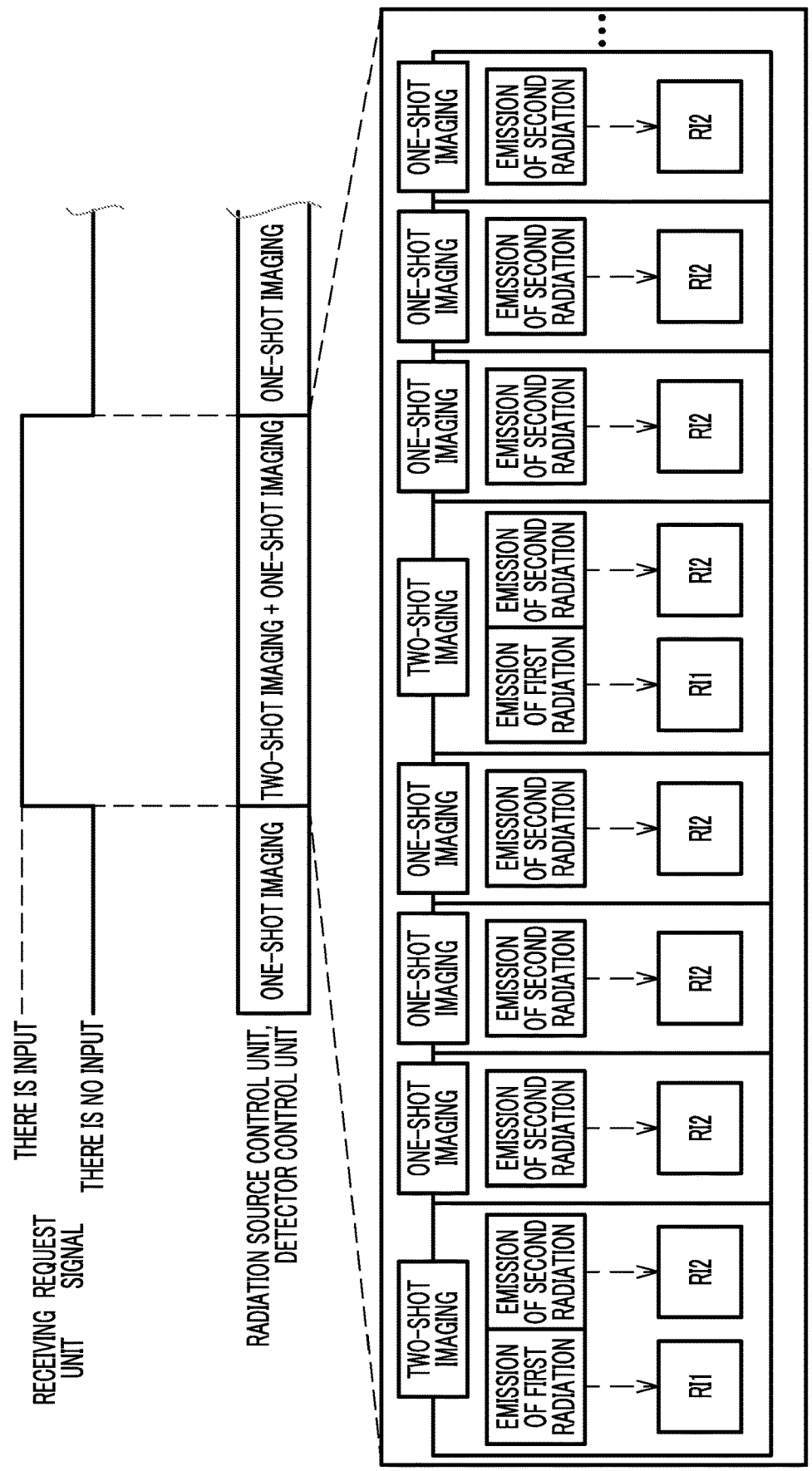
FIG. 26 is a diagram illustrating a fifth embodiment in which the two-shot imaging operation and the one-shot imaging operation are performed in a case in which the receiving unit receives the request signal.

In FIG. 26, in a moving image capture mode according to a fifth embodiment, in a case in which the receiving unit 77 receives the request signal RS, the two-shot imaging operation and the one-shot imaging operation are performed.

In FIG. 26, in a case in which four consecutive frames are viewed, the number of two-shot imaging operations is 1 and the number of one-shot imaging operations is 3. That is, the number of one-shot imaging operations is larger than the number of two-shot imaging operations. Further, in FIG. 26, one two-shot imaging operation is performed during three one-shot imaging operations. That is, one two-shot imaging operation is performed during a set number of one-shot imaging operations. The set number of imaging operations is not limited to 3 illustrated in FIG. 26, but may be 2 or 3 or more. Further, for example, a configuration in which the operator can change the setting of the set number of imaging operations may be used.

Figure 27:
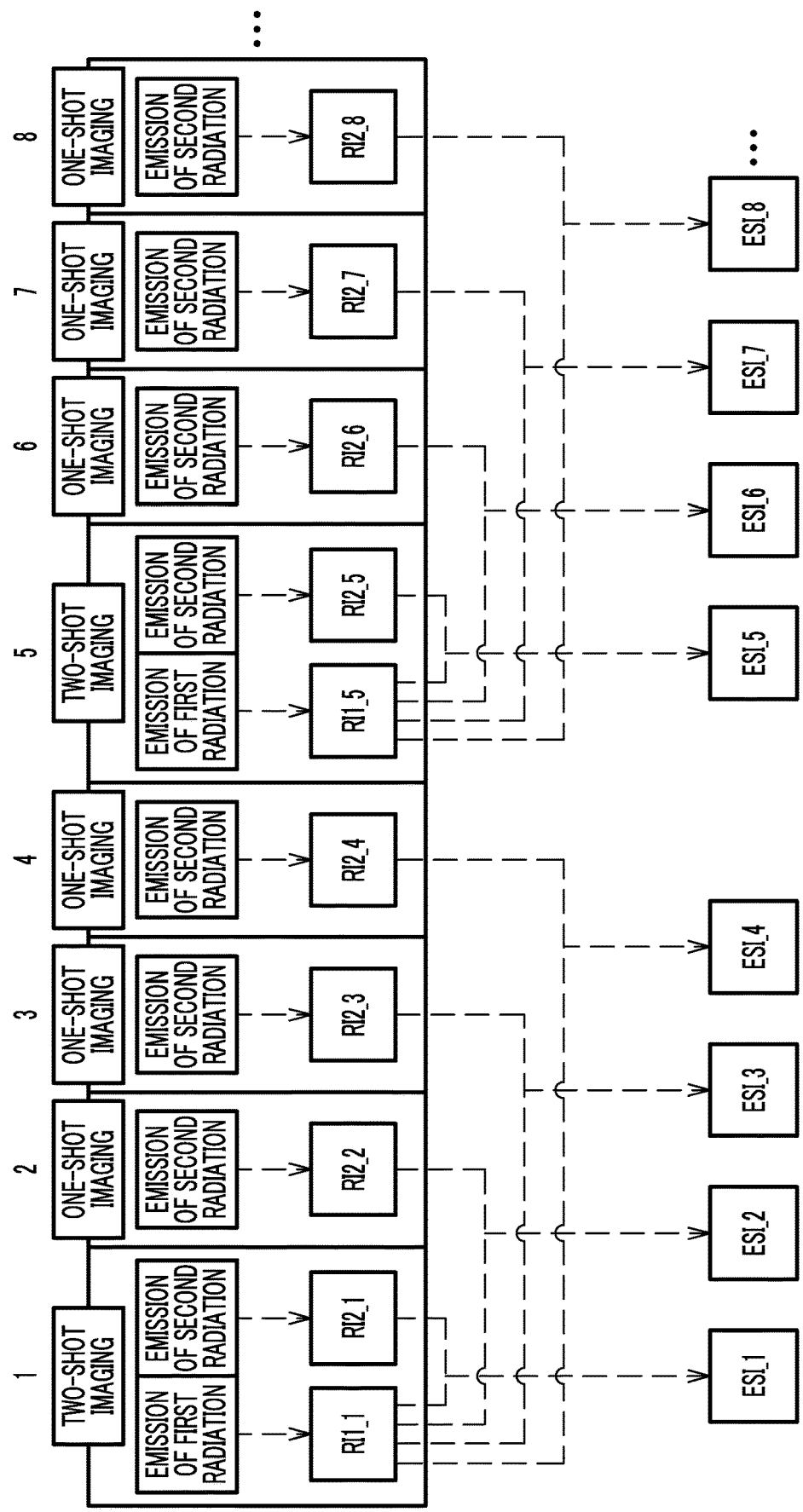
FIG. 27 is a diagram illustrating an energy subtraction image generation method in a case in which the two-shot imaging operation and the one-shot imaging operation are performed.

As illustrated in FIG. 27, the ES image ESI corresponding to the two-shot imaging operation is generated on the basis of the first radiographic image RI1 and the second radiographic image RI2 output from the radiation detector 11 in the two-shot imaging operation. For example, an ES image ESI_1 of frame 1 is generated on the basis of a first radiographic image RI1_1 and a second radiographic image RI2_1.

In contrast, the ES image ESI corresponding to the one-shot imaging operation is generated on the basis of one of the first radiographic image RI1 and the second radiographic image RI2 output from the radiation detector 11 in the one-shot imaging operation and the other of the first radiographic image RI1 and the second radiographic image RI2 output in the two-shot imaging operation immediately before the one-shot imaging operation.

In FIG. 27, as described above, "one of the first radiographic image RI1 and the second radiographic image RI2" is the second radiographic image RI2 and "the other of the first radiographic image RI1 and the second radiographic image RI2" is the first radiographic image RI1. Therefore, for example, an ES image ESI_2 of frame 2 is generated on the basis of the first radiographic image RI1_1 of frame 1 in the most recent two-shot imaging operation and the second radiographic image RI2_2. For example, an ES image ESI_8 of frame 8 is generated on the basis of a first radiographic image RI1_5 of frame 5 in the most recent two-shot imaging operation and a second radiographic image RI2_8.

As such, in the fifth embodiment, the radiation source control unit 56 and the detector control unit 57 perform the two-shot imaging operation and the one-shot imaging operation in a case in which the receiving unit 77 receives the request signal RS. Therefore, it is possible to further reduce the amount of radiation R and the amount of radiation exposure of the subject H, as compared to the fourth embodiment illustrated in FIG. 25 in which the two-shot imaging operation is performed in a case in which the receiving unit 77 receives the request signal RS. In addition, it is possible to further reduce the load applied to the radiation tube 15 and the radiation detector 11.

The ES image ESI corresponding to the two-shot imaging operation is generated on the basis of the first radiographic image RI1 and the second radiographic image RI2 output from the radiation detector 11 in the two-shot imaging operation. In contrast, the ES image ESI corresponding to the one-shot imaging operation is generated on the basis of one of the first radiographic image RI1 and the second radiographic image RI2 output from the radiation detector 11 in the one-shot imaging operation and the other of the first radiographic image RI1 and the second radiographic image RI2 output in the two-shot imaging operation immediately before the one-shot imaging operation. Therefore, it is possible to continuously acquire a plurality of ES images ESI without continuously performing the two-shot imaging operation a plurality of times. Further, in a case in which the ES image ESI corresponding to the one-shot imaging operation is generated, the other of the first radiographic image RI1 and the second radiographic image RI2 output in the most recent two-shot imaging operation is reused. Therefore, it is possible to reduce the load on the process of generating the ES images ESI.

In the examples illustrated in FIGS. 26 and 27, the number of one-shot imaging operations is larger than the number of two-shot imaging operations. Therefore, it is possible to further reduce the amount of radiation R, as compared to a case in which the number of two-shot imaging operations is equal to or larger than the number of one-shot imaging operations.

In the examples illustrated in FIGS. 26 and 27, one two-shot imaging operation is performed during a set number of one-shot imaging operations. Therefore, the two-shot imaging operation and the one-shot imaging operation may be regularly performed. It is possible to simply perform the radiation source control and the detector control.

In the examples illustrated in FIGS. 26 and 27, the radiation source control unit 56 performs control such that only the second radiation R2 with low intensity is emitted in the one-shot imaging operation. Therefore, it is possible to further reduce the amount of radiation R, as compared to a case in which only the first radiation R1 with high intensity is emitted. In a case in which only the first radiation R1 with high intensity is emitted, there is a high possibility that a residual image will be generated in the radiation detector 11 after the detection of the first radiographic image RI1. However, in a case in which the second radiation R2 with low intensity is used, there is a low possibility that a residual image will be generated. Therefore, it is possible to suppress the quality degradation of the second radiographic image RI2 due to the residual image and thus to suppress the quality degradation of the ES image ESI.

Figure 28:
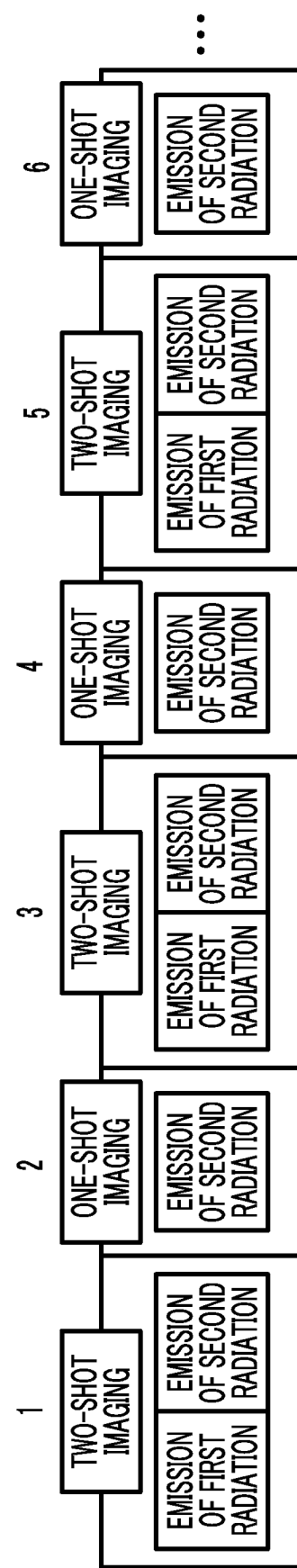
FIG. 28 is a diagram illustrating an example in which the two-shot imaging operation and the one-shot imaging operation are alternately performed.
Figure 29:
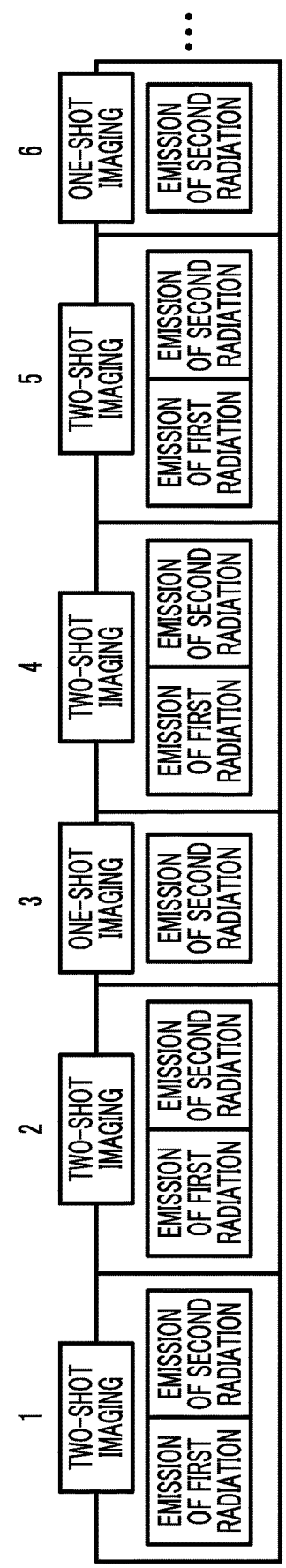
FIG. 29 is a diagram illustrating an example the one-shot imaging operation is performed once during a set number of two-shot imaging operations.

FIG. 28 illustrates an example in which the two-shot imaging operation and the one-shot imaging operation are alternately performed. FIG. 29 illustrates an example in which the one-shot imaging operation is performed once during a set number of (here, two) two-shot imaging operations. As such, the number of one-shot imaging operations may be equal to the number of two-shot imaging operations or the number of two-shot imaging operations may be larger than the number of one-shot imaging operations. The two-shot imaging operation may be performed only once at the beginning and then the one-shot imaging operation may be continuously performed a plurality of times, which is not illustrated. In short, any aspect may be used as long as it can reduce the amount of radiation R as compared to a case in which the two-shot imaging operation is continuously performed a plurality of times. In FIGS. 28 and 29, the first radiographic image RI1 and the second radiographic image RI2 are not illustrated.

FIG. 30 illustrates an aspect in which not the second radiation R2 but only the first radiation R1 is emitted in the one-shot imaging operation. In this case, the first radiation R1 is an example of "one of the first radiation and the second radiation" according to the technology of the present disclosure. In addition, the first radiographic image RI1 is an example of "one of the first radiographic image and the second radiographic image" according to the technology of the present disclosure. Conversely, the second radiographic image RI2 is an example of "the other of the first radiographic image and the second radiographic image" according to the technology of the present disclosure.

In the method of generating the ES image ESI, the first radiographic image RI1 and the second radiographic image RI2 in the example illustrated in FIG. 27 are reversed. For example, the ES image ESI_2 of frame 2 is generated on the basis of the second radiographic image RI2_1 of the frame 1 which is the most recent two-shot imaging operation and a first radiographic image RI1_2. Further, for example, an ES image ESI_8 of frame 8 is generated on the basis of a second radiographic image RI2_5 of frame 5 which is the most recent two-shot imaging operation and a first radiographic image RI1_8.

A configuration may be used in which the operator can select the fourth embodiment in which the two-shot imaging operation is performed in a case in which the receiving unit 77 receives the request signal RS and the fifth embodiment in which the two-shot imaging operation and the one-shot imaging operation are performed in a case in which the receiving unit 77 receives the request signal RS.

The cold cathode is not limited to the field emission type. The cold cathode may be any type other than the thermal electron emission type. Further, the cathode 30 is not limited to the cold cathode and may be a hot cathode.

For example, the following imaging modes may be used: an imaging mode for performing the ES imaging according to the related art which is completed by one two-shot imaging operation; and an imaging mode for simply acquiring a still radiographic image instead of the ES imaging.

In the two-shot imaging operation, first, the second radiation R2 may be emitted and the second radiographic image RI2 may be output. Then, the first radiation R1 may be emitted and the first radiographic image RI1 may be output.

The control device 13 and the console 14 may be integrated into one device. Further, the control device 13 may be divided into a radiation source control device that controls the operation of the radiation source 10 and a detector control device that controls the operation of the radiation detector 11. The radiation source control unit 56 may be provided in the radiation source control device and the detector control unit 57 may be provided in the detector control device.

The hardware configuration of the computer forming the console 14 can be modified in various ways. For example, the console 14 may be configured by a plurality of computers that are separated as hardware in order to improve processing performance and reliability. Specifically, the functions of the acquisition unit 75 and the detection unit 76 and the functions of the receiving unit 77, the generation unit 78, and the display control unit 79 are distributed to two computers. In this case, the console 14 is configured by two computers.

As such, the hardware configuration of the computer forming the console 14 can be appropriately changed according to the required performance, such as processing capability, safety, and reliability. Further, not only the hardware but also application programs, such as the operation programs 53 and 70, may be duplicated or dispersively stored in a plurality of storage devices in order to ensure safety and reliability.

In each of the above-described embodiments, for example, the following various processors can be used as the hardware structure of processing units performing various processes, such as the irradiation condition acquisition unit 55, the radiation source control unit 56, the detector control unit 57, the image transmission unit 58, the acquisition unit 75, the detection unit 76, the receiving unit 77, the generation unit 78, and the display control unit 79. The various processors include a programmable logic device (PLD), such as a field programmable gate array (FPGA), which is a processor whose circuit configuration can be changed after manufacture and a dedicated electric circuit, such as an application specific integrated circuit (ASIC), which is a processor having a dedicated circuit configuration designed to perform a specific process, in addition to the CPUs 52 and 62 which are general-purpose processors executing software to function as various processing units.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to understand the invention described in the following Supplementary Note 1 from the above description.

Supplementary Note 1

There is provided a radiography apparatus comprising a radiation source that emits radiation and a radiation detector that detects the radiation transmitted through a subject and outputs a radiographic image of the subject. The radiography apparatus comprises: a radiation source control processor that performs control to direct the radiation source to continuously emit the radiation in order to perform a moving image capture mode which continuously acquires a plurality of the radiographic images required for displaying a moving image according to a preset frame interval; a detector control processor that performs control to direct the radiation detector to continuously output the radiographic image based on the radiation in a case in which the moving image capture mode is performed; an acquisition processor that acquires the radiographic image; a receiving processor that receives a request signal to request generation of an energy subtraction image in which a structure in the subject has been highlighted and which is referred to for diagnosis; and a generation processor that generates the energy subtraction image on the basis of the radiographic image acquired by the acquisition processor during the moving image capture mode, does not generate the energy subtraction image in a case in which the receiving processor does not receive the request signal, and generates the energy subtraction image in a case in which the receiving processor receives the request signal.

In addition, the technology according to the present disclosure includes the invention described in the following Supplementary Notes 2 to 5.

Supplementary Note 2

There is provided an image processing apparatus comprising: an acquisition unit that acquires a radiographic image continuously output from a radiation detector by directing a radiation source to continuously emit radiation in order to perform a moving image capture mode which continuously acquires a plurality of the radiographic images required for displaying a moving image according to a preset frame interval; a receiving unit that receives a request signal to request generation of an energy subtraction image in which a structure in a subject has been highlighted and which is referred to for diagnosis; and a generation unit that generates the energy subtraction image on the basis of the radiographic image acquired by the acquisition unit during the moving image capture mode, does not generate the energy subtraction image in a case in which the receiving unit does not receive the request signal, and generates the energy subtraction image in a case in which the receiving unit receives the request signal.

Supplementary Note 3

There is provided a method for operating an image processing apparatus. The method comprises: an acquisition step of acquiring a radiographic image continuously output from a radiation detector by directing a radiation source to continuously emit radiation in order to perform a moving image capture mode which continuously acquires a plurality of the radiographic images required for displaying a moving image according to a preset frame interval; a receiving step of receiving a request signal to request generation of an energy subtraction image in which a structure in a subject has been highlighted and which is referred to for diagnosis; a generation step of generating the energy subtraction image on the basis of the radiographic image acquired in the acquisition step during the moving image capture mode and generating the energy subtraction image in a case in which the receiving unit receives the request signal; and a non-generation step of not generating the energy subtraction image in a case in which the receiving unit does not receive the request signal.

Supplementary Note 4

There is provided a program for operating an image processing apparatus. The program causes a computer to function as: an acquisition unit that acquires a radiographic image continuously output from a radiation detector by directing a radiation source to continuously emit radiation in order to perform a moving image capture mode which continuously acquires a plurality of the radiographic images required for displaying a moving image according to a preset frame interval; a receiving unit that receives a request signal to request generation of an energy subtraction image in which a structure in a subject has been highlighted and which is referred to for diagnosis; and a generation unit that generates the energy subtraction image on the basis of the radiographic image acquired by the acquisition unit during the moving image capture mode, does not generate the energy subtraction image in a case in which the receiving unit does not receive the request signal, and generates the energy subtraction image in a case in which the receiving unit receives the request signal.

Supplementary Note 5

There is provided an image processing apparatus comprising: an acquisition processor that acquires a radiographic image continuously output from a radiation detector by directing a radiation source to continuously emit radiation in order to perform a moving image capture mode which continuously acquires a plurality of the radiographic images required for displaying a moving image according to a preset frame interval; a receiving processor that receives a request signal to request generation of an energy subtraction image in which a structure in a subject has been highlighted and which is referred to for diagnosis; and a generation processor that generates the energy subtraction image on the basis of the radiographic image acquired by the acquisition processor during the moving image capture mode, does not generate the energy subtraction image in a case in which the receiving processor does not receive the request signal, and generates the energy subtraction image in a case in which the receiving processor receives the request signal.

The console 14 according to each of the above-described embodiments is an example of the "image processing apparatus" described in Supplementary Notes 2 to 5. In addition, the operation program 70 is an example of the "program for operating an image processing apparatus" described in Supplementary Note 4.

In the technology according to the present disclosure, the above-mentioned various embodiments and various modification examples may be combined with each other. In addition, the present disclosure is not limited to each of the above-described embodiments and various configurations can be used without departing from the scope and spirit of the present disclosure. Further, the technology according to the present disclosure may be applied to a storage medium that non-temporarily stores the program in addition to the program.

The contents described and illustrated above are the detailed description of portions related to the technology according to the present disclosure and are merely examples of the technology according to the present disclosure. For example, the description of the configurations, the functions, the operations, and the effects is the description of an example of the configurations, functions, operations, and effects of a portion according to the technology of the present disclosure. Therefore, for the contents described and illustrated above, unnecessary portions may be deleted or new elements may be added or replaced without departing from the scope and spirit of the technology according to the present disclosure. In the contents described and illustrated above, the description of common technical knowledge that does not require any explanation in order to enable the implementation of the technology according to the present disclosure is omitted in order to avoid complications and to facilitate the understanding of the portions related to the technology according to the present disclosure.

All of the documents, the patent applications, and the technical standards described in the specification are incorporated by reference to the same extent as the incorporation of each of the documents, the patent applications and the technical standards by reference is specifically and individually stated.

What is claimed is:

1. A radiography apparatus comprising:
   a radiation source that emits radiation;
   a radiation detector that detects the radiation transmitted through a subject and outputs a radiographic image of the subject;
   a radiation source control unit that performs control to direct the radiation source to continuously emit the radiation in order to perform a moving image capture mode which continuously acquires a plurality of the radiographic images required for displaying a moving image according to a preset frame interval;
   a detector control unit that performs control to direct the radiation detector to continuously output the radiographic image based on the radiation in a case in which the moving image capture mode is performed;
   an acquisition unit that acquires the radiographic image;
   a receiving unit that receives a request signal to request generation of an energy subtraction image in which a structure in the subject has been highlighted and which is referred to for diagnosis; and
   a generation unit that generates the energy subtraction image on the basis of the radiographic image acquired by the acquisition unit during the moving image capture mode, does not generate the energy subtraction image in a case in which the receiving unit does not receive the request signal, and generates the energy subtraction image in a case in which the receiving unit receives the request signal.

2. The radiography apparatus according to claim 1,
wherein the moving image capture mode includes directing the radiation source to emit first radiation with a first energy distribution and second radiation with a second energy distribution different from the first energy distribution and directing the radiation detector to output a first radiographic image based on the first radiation and a second radiographic image based on the second radiation, and
the generation unit generates the energy subtraction image on the basis of the first radiographic image and the second radiographic image.

3. The radiography apparatus according to claim 2, further comprising:
a detection unit that detects whether or not a contrast agent has been administered to the subject and outputs the request signal to the receiving unit in a case in which it is detected that contrast agent has been administered.

4. The radiography apparatus according to claim 2, further comprising:
an operation unit that outputs the request signal to the receiving unit in response to an operation command from an operator.

5. The radiography apparatus according to claim 2,
wherein an average value of generation intervals of the energy subtraction image is greater than the frame interval.

6. The radiography apparatus according to claim 2, further comprising:
a display control unit that performs control to display the energy subtraction image and at least one of the first radiographic image or the second radiographic image.

7. The radiography apparatus according to claim 2,
wherein, in the moving image capture mode, a one-shot imaging operation which directs the radiation source to emit only one of the first radiation and the second radiation and directs the radiation detector to output only one of the first radiographic image and the second radiographic image is performed in a case in which the receiving unit does not receive the request signal.

8. The radiography apparatus according to claim 7,
wherein, in the moving image capture mode, a two-shot imaging operation which directs the radiation source to continuously emit the first radiation and the second radiation and directs the radiation detector to output the first radiographic image and the second radiographic image is performed in a case in which the receiving unit receives the request signal.

9. The radiography apparatus according to claim 7,
wherein, in the moving image capture mode, the one-shot imaging operation and the two-shot imaging operation which directs the radiation source to continuously emit the first radiation and the second radiation and directs the radiation detector to output the first radiographic image and the second radiographic image are performed in a case in which the receiving unit receives the request signal.

10. The radiography apparatus according to claim 9,
wherein the generation unit generates the energy subtraction image corresponding to the two-shot imaging operation on the basis of the first radiographic image and the second radiographic image output from the radiation detector in the two-shot imaging operation and generates the energy subtraction image corresponding to the one-shot imaging operation on the basis of one of the first radiographic image and the second radiographic image output from the radiation detector in the one-shot imaging operation and the other of the first radiographic image and the second radiographic image output from the radiation detector in the two-shot imaging operation immediately before the one-shot imaging operation.

11. The radiography apparatus according to claim 7,
wherein an intensity of the second radiation in the second energy distribution is lower than an intensity of the first radiation in the first energy distribution, and
the radiation source control unit directs the radiation source to emit only the second radiation in the one-shot imaging operation.

12. The radiography apparatus according to claim 2,
wherein the radiation source includes a radiation tube having a cold cathode.

13. The radiography apparatus according to claim 12,
wherein the cold cathode is a field emission type having an electron emission source that emits an electron beam using a field emission phenomenon.

14. The radiography apparatus according to claim 12,
wherein at least two radiation tubes of a first radiation tube that generates the first radiation and a second radiation tube that generates the second radiation are provided as the radiation tube.

15. A method for operating a radiography apparatus comprising a radiation source that emits radiation and a radiation detector that detects the radiation transmitted through a subject and outputs a radiographic image of the subject, the method comprising:
a radiation source control step of performing control to direct the radiation source to continuously emit the radiation in order to perform a moving image capture mode which continuously acquires a plurality of the radiographic images required for displaying a moving image according to a preset frame interval;
a detector control step of performing control to direct the radiation detector to continuously output the radiographic image based on the radiation in a case in which the moving image capture mode is performed;
an acquisition step of acquiring the radiographic image;
a receiving step of receiving a request signal to request generation of an energy subtraction image in which a structure in the subject has been highlighted and which is referred to for diagnosis;
a generation step of generating the energy subtraction image on the basis of the radiographic image acquired in the acquisition step during the moving image capture mode and generating the energy subtraction image in a case in which the request signal is received in the receiving step; and
a non-generation step of not generating the energy subtraction image in a case in which the request signal is not received in the receiving step.

16. A non-transitory computer-readable storage medium storing a program for operating a radiography apparatus comprising a radiation source that emits radiation and a radiation detector that detects the radiation transmitted through a subject and outputs a radiographic image of the subject, the program causing a computer to function as:
a radiation source control unit that performs control to direct the radiation source to continuously emit the radiation in order to perform a moving image capture mode which continuously acquires a plurality of the radiographic images required for displaying a moving image according to a preset frame interval;

a detector control unit that performs control to direct the radiation detector to continuously output the radiographic image based on the radiation in a case in which the moving image capture mode is performed;

an acquisition unit that acquires the radiographic image;

a receiving unit that receives a request signal to request generation of an energy subtraction image in which a structure in the subject has been highlighted and which is referred to for diagnosis; and a generation unit that generates the energy subtraction image on the basis of the radiographic image acquired by the acquisition unit during the moving image capture mode, does not generate the energy subtraction image in a case in which the receiving unit does not receive the request signal, and generates the energy subtraction image in a case in which the receiving unit receives the request signal.

* * * * *